(12) United States Patent
Sakata et al.

(10) Patent No.: US 12,165,321 B2
(45) Date of Patent: Dec. 10, 2024

(54) MEDICAL IMAGE PROCESSING DEVICE, STORAGE MEDIUM, MEDICAL DEVICE, AND TREATMENT SYSTEM

(71) Applicant: Toshiba Energy Systems & Solutions Corporation, Kawasaki (JP)

(72) Inventors: Yukinobu Sakata, Kawasaki (JP); Ryusuke Hirai, Meguro (JP); Akiyuki Tanizawa, Kawasaki (JP); Kyoka Sugiura, Kawasaki (JP); Shinichiro Mori, Chiba (JP); Keiko Okaya, Setagaya (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 370 days.

(21) Appl. No.: 17/583,678

(22) Filed: Jan. 25, 2022

(65) Prior Publication Data
US 2022/0148180 A1    May 12, 2022

Related U.S. Application Data

(63) Continuation of application No. PCT/JP2020/037994, filed on Oct. 7, 2020.

(30) Foreign Application Priority Data

Oct. 10, 2019  (JP) ................................ 2019-186737

(51) Int. Cl.
*G06T 7/00*     (2017.01)
*A61B 6/00*     (2024.01)
(Continued)

(52) U.S. Cl.
CPC .............. *G06T 7/0014* (2013.01); *A61B 6/04* (2013.01); *G06T 7/74* (2017.01); *G06T 2207/10081* (2013.01); *G06T 2207/10121* (2013.01)

(58) Field of Classification Search
None
See application file for complete search history.

(56) References Cited

U.S. PATENT DOCUMENTS 6,662,036 B2 * 12/2003 Cosman ............... A61B 6/5247
600/417
2012/0051624 A1 * 3/2012 Ando ..................... G06T 7/593
382/154

(Continued)

FOREIGN PATENT DOCUMENTS

CN    111839555 B  * 10/2023  ........... A61B 5/0037
EP    3589365 B1   *  1/2023  ........... A61N 5/1048
(Continued)

OTHER PUBLICATIONS

Korean Notice of Allowance dated Aug. 29, 2024, issued in Korean Patent Application No. 10-2022-7004709 (with English translation).

*Primary Examiner* — Mohammed Rachedine
(74) *Attorney, Agent, or Firm* — Oblon, McClelland, Maier & Neustadt, L.L.P.

(57) ABSTRACT

A medical image processing device of an embodiment includes a comparator and a position determination region determiner. The comparator compares a first image obtained by photographing a patient with a comparative image which is an image used in previous radiation treatment and in which a valid region used in position alignment in the radiation treatment is designated. The position determination region determiner determines a position determination region similar to the valid region included within the first image on the basis of a comparison result of the comparator.

10 Claims, 14 Drawing Sheets

(51) Int. Cl.
  *A61B 6/03*   (2006.01)
  *A61B 6/04*   (2006.01)
  *A61B 6/46*   (2024.01)
  *A61B 6/50*   (2024.01)
  *A61N 5/10*   (2006.01)
  *G06T 7/73*   (2017.01)

(56) References Cited

U.S. PATENT DOCUMENTS

2015/0087881 A1* 3/2015 Miyamoto ........... A61N 5/1037
                                                        600/1
2018/0184987 A1* 7/2018 Ishihara .................. A61B 5/05

FOREIGN PATENT DOCUMENTS

| JP | 2012-24145 A | 2/2012 |
| JP | 2013-111156 A | 6/2013 |
| JP | 2013-192702 A | 9/2013 |
| JP | 6095112 B2 | 3/2017 |
| KR | 101617773 B1 * | 6/2014 |
| KR | 10-2017-0000344 A | 1/2017 |
| KR | 10-2018-0036776 A | 4/2018 |
| KR | 10-2019-0074976 A | 6/2019 |
| KR | 10-2019-0074977 A | 6/2019 |
| WO | WO 2017/037904 A1 | 3/2017 |

* cited by examiner

CTI-B

CTI-C

−40 DEGREES            40 DEGREES

CTI-A

MEDICAL IMAGE PROCESSING DEVICE, STORAGE MEDIUM, MEDICAL DEVICE, AND TREATMENT SYSTEM

CROSS-REFERENCE TO RELATED APPLICATION

This application is based upon and claims the benefit of priority from Japanese Patent Application No. 2019-186737, filed Oct. 10, 2019 and PCT/JP2020/037994, filed Oct. 7, 2020; the entire contents all of which are incorporated herein by reference.

FIELD

Embodiments of the present invention relate to a medical image processing device, a storage medium, a medical device, and a treatment system.

BACKGROUND

Radiation treatment is a treatment method of irradiating a lesion within a patient's body with radiation to destroy the lesion. In the radiation treatment, it is necessary to accurately radiate the radiation to a position of the lesion because normal tissue within the patient's body that is irradiated with the radiation may be affected. Thus, when the radiation treatment is performed, computed tomography (CT) is first performed, for example, in advance in a treatment planning stage, and the position of the lesion within the patient's body is three-dimensionally ascertained. The radiation irradiation direction and the radiation irradiation intensity are planned on the basis of the ascertained position of the lesion. Thereafter, the position of the patient in a treatment stage is aligned with a position of the patient planned in the treatment planning stage and a lesion is irradiated with radiation in accordance with an irradiation direction or an irradiation intensity planned in the treatment planning stage.

In the related art, technology related to a radiation treatment system that employs a method of improving the accuracy of position determination using a valid region of interest in a position determination process of aligning a position of a patient in radiation treatment has been disclosed (see, for example, Patent Document 1). In the related art, the position of the patient is determined by integrating a position determination result in the entire image and a position determination result based on a feature quantity related to a region of interest input in a treatment plan.

DETAILED DESCRIPTION

A medical image processing device of an aspect of the present embodiment includes a comparator and a position determination region determiner. The comparator compares a first image obtained by photographing a patient with a comparative image which is an image used in previous radiation treatment and in which a valid region used in position alignment in the radiation treatment is designated. The position determination region determiner determines a position determination region similar to the valid region included within the first image on the basis of a comparison result of the comparator.

Hereinafter, a medical image processing device, a storage medium, a medical device, and a treatment system of embodiments will be described with reference to the drawings.

First Embodiment

Figure 1:
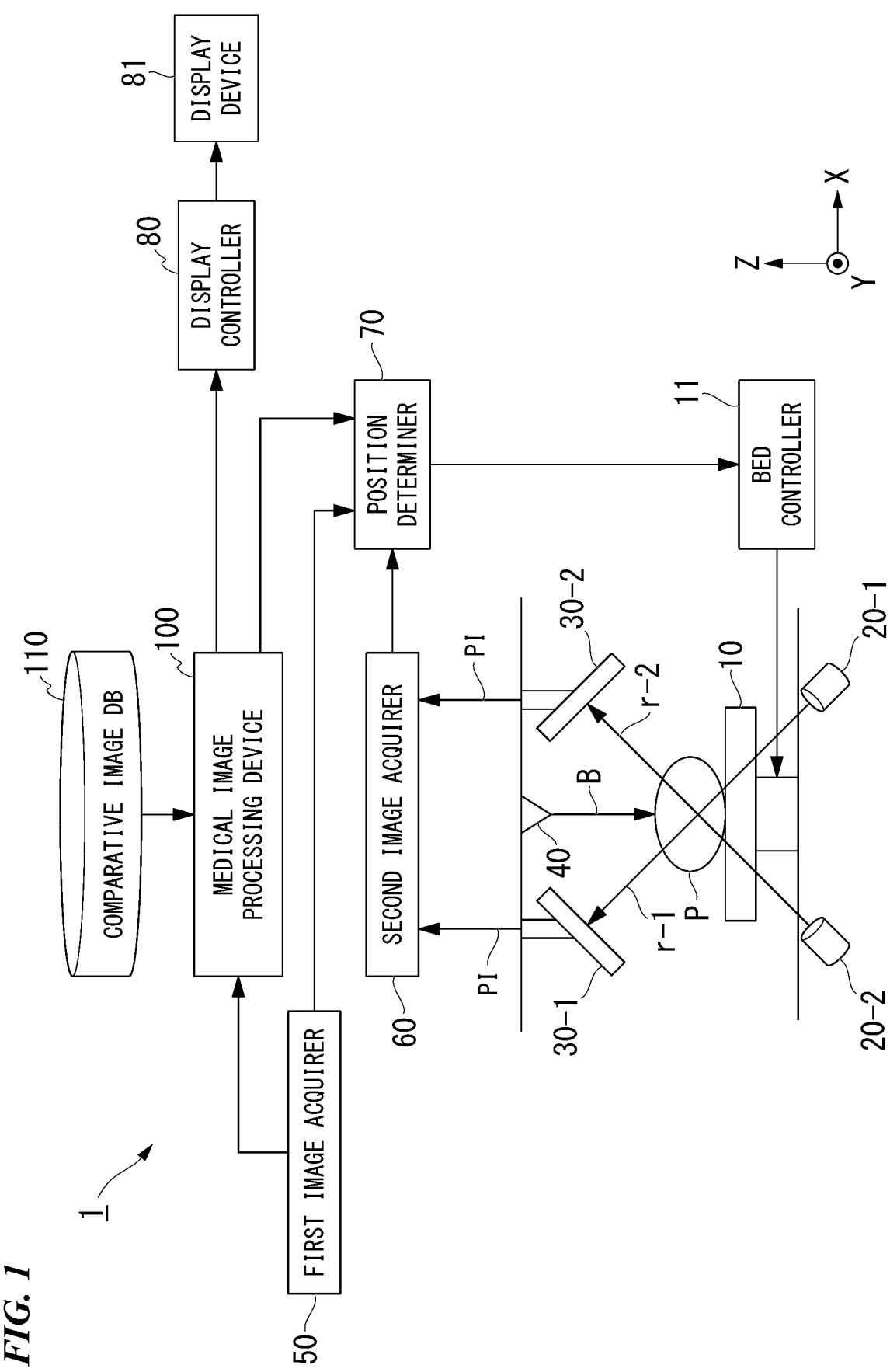
FIG. 1 is a block diagram showing a schematic configuration of a treatment system provided with a medical device including a medical image processing device of a first embodiment.

FIG. 1 is a block diagram showing a schematic configuration of a treatment system provided with a medical device including a medical image processing device of a first embodiment. The treatment system 1 includes, for example, a treatment table 10, a bed controller 11, two radiation sources 20 (a radiation source 20-1 and a radiation source 20-2), two radiation detectors 30 (a radiation detector 30-1 and a radiation detector 30-2), a treatment beam irradiation gate 40, a first image acquirer 50, a second image acquirer 60, a position determiner 70, a display controller 80, a display device 81, a medical image processing device 100, and a comparative image database (DB) 110.

Also, a hyphen "-" indicated after a reference numeral shown in FIG. 1 and a number subsequent to the hyphen are used for identifying a corresponding relationship. For example, in the corresponding relationship between the radiation source 20 and the radiation detector 30, a state in which the radiation source 20-1 and the radiation detector 30-1 correspond to each other to form one set is shown and a state in which the radiation source 20-2 and the radiation detector 30-2 correspond to each other to form another set is shown. In the following description, when a plurality of identical components are represented without being distinguished, they are represented without the hyphen "-" and the number subsequent to the hyphen.

The treatment table 10 is a bed on which a subject (a patient) P that will undergo radiation treatment is fixed. The bed controller 11 controls a translation mechanism and a rotation mechanism provided on the treatment table 10 so that a direction in which the patient P fixed on the treatment table 10 is irradiated with the treatment beam is changed. The bed controller 11 controls, for example, each of the translation mechanism and the rotation mechanism of the treatment table 10 in three axial directions, i.e., in six axial directions.

The radiation source 20-1 radiates radiation r-1 for seeing through the body of the patient P at a predetermined angle. The radiation source 20-2 radiates radiation r-2 for seeing through the body of the patient P at a predetermined angle different from that of the radiation source 20-1. The radiation r-1 and the radiation r-2 are, for example, X-rays. In FIG. 1, a case in which X-ray photography is performed from two directions on the patient P fixed on the treatment table 10 is shown. Also, the illustration of a controller that controls the irradiation with the radiation r by the radiation source 20 is omitted from FIG. 1.

The radiation detector 30-1 detects the radiation r-1 which has been radiated from the radiation source 20-1 and has arrived at the radiation detector 30-1 after passing through the inside of the body of the patient P and generates an X-ray fluoroscopic image PI of the inside of the body of the patient P according to a magnitude of energy of the detected radiation r-1. The radiation detector 30-2 detects the radiation r-2 which has been radiated from the radiation source 20-2 and has arrived at the radiation detector 30-2 after passing through the inside of the body of the patient P and generates an X-ray fluoroscopic image PI of the inside of the body of the patient P according to a magnitude of energy of the detected radiation r-2. The radiation detectors 30 are X-ray detectors arranged in a two-dimensional array shape and generate a digital image in which a magnitude of energy of the radiation r arriving at each X-ray detector is represented by a digital value as an X-ray fluoroscopic image PI. The radiation detector 30 is, for example, a flat panel detector (FPD), an image intensifier, or a color image intensifier. In the following description, each radiation detector 30 is assumed to be an FPD. The radiation detector 30 (the FPD) outputs the generated X-ray fluoroscopic image PI to the medical image processing device 100. Also, the illustration of a controller that controls the generation of the X-ray fluoroscopic image PT by the radiation detector 30 is omitted from FIG. 1.

In the treatment system 1, a set of the radiation source 20 and the radiation detector 30 is an example of a "photography device" in the claims. In FIG. 1, a photography device, which captures X-ray fluoroscopic images PI of the patient P from two different directions, is shown. Although a configuration including two sets of radiation sources 20 and radiation detectors 30, i.e., two photography devices, in the treatment system 1 shown in FIG. 1 is shown, the number of photography devices provided in the treatment system 1 is not limited to two. For example, the treatment system 1 may include three or more photography devices (three or more sets of radiation sources 20 and radiation detectors 30). Also, the treatment system 1 may include only one photography device (a set of a radiation source 20 and a radiation detector 30).

The treatment beam irradiation gate 40 irradiates the patient P with radiation for destroying a lesion, which is a treatment target portion in the body of the patient P, as the treatment beam B. The treatment beam B is, for example, X-rays, γ-rays, an electron beam, a proton beam, a neutron beam, a heavy particle beam, or the like. The treatment beam B is linearly radiated from the treatment beam irradiation gate 40 to the patient P (more specifically, the lesion in the body of the patient P). For example, a treatment beam irradiation controller (not shown) controls the irradiation with the treatment beam B by the treatment beam irradiation gate 40. In the treatment system 1, the treatment beam irradiation gate 40 is an example of an "irradiator" in the claims.

Although a configuration including one fixed treatment beam irradiation gate 40 is shown in the treatment system 1 shown in FIG. 1, the present invention is not limited thereto and the treatment system 1 may include a plurality of treatment beam irradiation gates. For example, the treatment system 1 may further include a treatment beam irradiation gate that irradiates the patient P with the treatment beam from a horizontal direction. Also, the treatment system 1 may be configured to irradiate the patient P with treatment beams from various directions by rotating one treatment beam irradiation gate around the patient P. For example, the treatment beam irradiation gate 40 shown in FIG. 1 may be configured to be able to rotate 360 degrees with respect to a rotation axis in a horizontal direction Y shown in FIG. 1. The treatment system 1 having the above configuration is called a rotary gantry type treatment system. Also, in the rotary gantry type treatment system, the radiation source 20 and the radiation detector 30 also rotate 360 degrees at the same time with respect to an axis that is the same as the rotation axis of the treatment beam irradiation gate 40.

In the treatment system 1, a combination of the first image acquirer 50, the second image acquirer 60, the position determiner 70, the display controller 80, and the medical image processing device 100 is an example of a "medical device" in the claims. Also, for example, a hardware processor such as a central processing unit (CPU) and a storage device (a storage device including a non-transitory storage medium) storing a program (software) are provided for some or all of the functions of the components provided in the medical device and the functions of the components may be implemented by the processor executing the program. Also, some or all of the functions of the components provided in the above-described medical device may be implemented by hardware (including a circuit unit; circuitry) such as a large-scale integration (LSI) circuit, an application-specific integrated circuit (ASIC), a field-programmable gate array (FPGA), or a graphics processing unit (GPU) or the functions of the components may be implemented by software and hardware in cooperation. Also, some or all of the functions of the components provided in the medical device may be implemented by a dedicated LSI circuit. Here, the program (software) may be pre-stored in a storage device (a storage device including a non-transitory storage medium) provided in the treatment system 1 such as a read only memory (ROM), a random-access memory (RAM), a hard disk drive (HDD), or a flash memory or may be stored in a removable storage medium (a non-transitory storage medium) such as a DVD or a CD-ROM and installed in the storage device provided in the treatment system 1 when the storage medium is mounted in a drive device provided in the treatment system 1. Also, the program (software) may be downloaded in advance from another computer device via the network and installed in the storage device provided in the treatment system 1.

The first image acquirer 50 acquires a three-dimensional volume image for seeing through the body of the patient P of the treatment target. The three-dimensional volume image is, for example, a three-dimensional image acquired by photographing the patient P with a photography device such as a CT device, a cone-beam (CB) CT device, a magnetic resonance imaging (MRI) device, or an ultrasonic diagnostic device. In relation to the three-dimensional volume image, for example, the position of the treatment portion, the orientation in which the treatment portion is irradiated with the treatment beam B (an irradiation direction), the intensity of the treatment beam B to be radiated (an irradiation intensity), and the like are predetermined with respect to the CT image obtained by photographing the patient P at the planning stage before the radiation treatment is performed such as the stage of the treatment planning in the radiation treatment. The three-dimensional volume image may be, for example, a digitally reconstructed radiograph (DRR) image obtained by virtually reconstructing the X-ray fluoroscopic image PI from the CT image. In the following description, it is assumed that the first image acquirer 50 acquires a CT image. The first image acquirer 50 outputs the acquired CT image to the position determiner 70 and the medical image processing device 100. Also, the CT image may include a region of interest (ROI) when radiation treatment is performed. The three-dimensional volume image (for example, the CT image) or the DRR image acquired by the first image acquirer 50 is an example of a "first image" in the claims.

The medical image processing device 100 determines a position determination region for use in position alignment of the patient P with respect to the CT image output by the first image acquirer 50 with reference to the comparative image collected in the comparative image database 110. Also, the medical image processing device 100 may acquire, for example, a comparative image collected in the comparative image database 110 via a local area network (LAN) or a wide area network (WAN) and determine the position determination region with respect to the CT image with reference to the acquired comparative image. The medical image processing device 100 outputs information of the determined position determination region to the position determiner 70. Also, the medical image processing device 100 outputs the CT image output by the first image acquirer 50 and the information of the determined position determination region to the display controller 80. Details regarding the configuration and process of the medical image processing device 100 will be described below.

In the comparative image database 110, a comparative image generated from a three-dimensional volume image (for example, a CT image) used in position alignment of a patient in previous radiation treatment is collected. In the comparative image database 110, a plurality of comparative images are collected for each treatment portion treated in the previous radiation treatment. In other words, in the comparative image database 110, an image group of comparative images for each treatment portion is collected. The comparative image collected in the comparative image database 110 may be a three-dimensional image or a two-dimensional image. Details regarding the configuration of the comparative images collected in the comparative image database 110 will be described below.

The second image acquirer 60 acquires an X-ray fluoroscopic image PI of the inside of the body of the current patient P fixed on the treatment table 10 in a treatment room where the treatment system 1 is installed. The second image acquirer 60 acquires an X-ray fluoroscopic image PI of the inside of the body of the patient P currently fixed on the treatment table 10 using each radiation detector 30. That is, the second image acquirer 60 acquires the X-ray fluoroscopic image PI of the patient P photographed at a time point different from that of the CT image acquired by the first image acquirer 50. Also, the second image acquirer 60 and the radiation detector 30 may be configured to be connected through a LAN or a WAN. The second image acquirer 60 outputs the acquired X-ray fluoroscopic image PI to the position determiner 70. The X-ray fluoroscopic image PI is an example of a "second image" in the claims.

The position determiner 70 collates the CT image output by the first image acquirer 50 with the X-ray fluoroscopic image PI output by the second image acquirer 60 on the basis of information of the position determination region output by the medical image processing device 100 and determines a position of the patient P suitable for performing radiation treatment. The position determiner 70 obtains the amount of movement of the treatment table 10 for moving the current position of the patient P fixed on the treatment table 10 to the position suitable for performing radiation treatment. In other words, the position determiner 70 obtains the amount of movement of the treatment table 10 required to irradiate the treatment portion with the treatment beam B from an irradiation direction predetermined for the CT image at the planning stage at the current position of the patient P. The position determiner 70 outputs information of the obtained amount of movement to the bed controller 11 and causes the position of the patient P to be moved by the translation mechanism and the rotation mechanism provided in the treatment table 10.

The display controller 80 causes the display device 81 to display an image obtained by superimposing the position determination region determined by the medical image processing device 100 on the CT image output by the medical image processing device 100. Thereby, for example, the display device 81 such as a liquid crystal display (LCD) displays the range of the position determination region within the CT image and a radiation treatment practitioner (a doctor or the like) who uses the treatment system 1 can visually confirm the position determination region that has been determined. For example, the treatment system 1 may be configured to include a user interface such as an operator (not shown) operated by the radiation treatment practitioner (the doctor or the like), and to be able to manually adjust the position determination region determined by the medical image processing device 100. Also, in the treatment system 1, the "medical device" may be configured to include the user interface such as the operator (not shown) in addition to the first image acquirer 50, the second image acquirer 60, the position determiner 70, the display controller 80, and the medical image processing device 100 as described above. Also, in the treatment system 1, the "medical device" may be configured to be further integrated with the display device 81.

Figure 2:
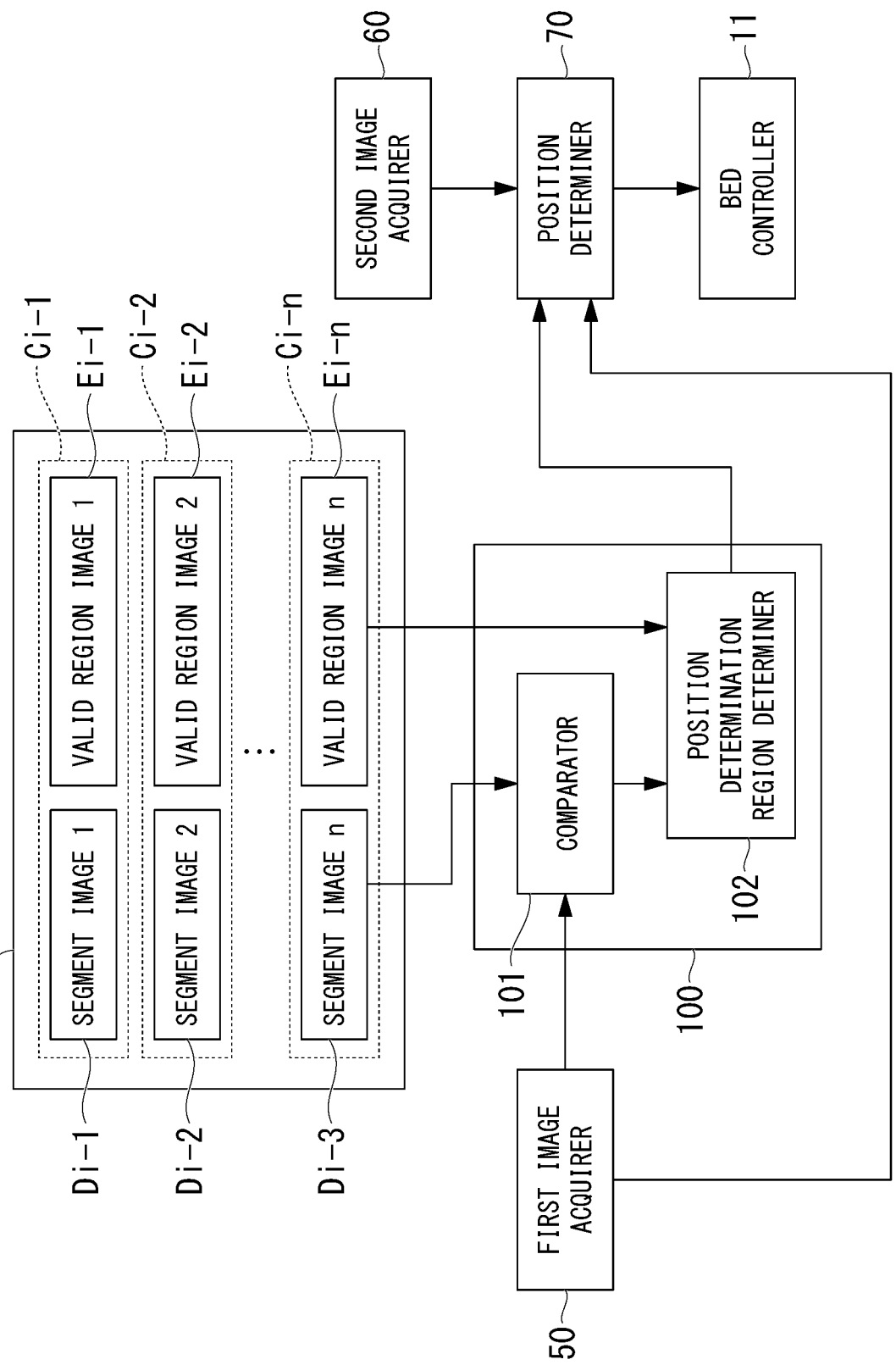
FIG. 2 is a block diagram showing a schematic configuration of the medical device and the medical image processing device of the first embodiment.

Next, a configuration of the medical device including the medical image processing device 100 of the first embodiment constituting the treatment system 1 will be described. FIG. 2 is a block diagram showing a schematic configuration of the medical device and the medical image processing device 100 of the first embodiment. Connection relationships between the first image acquirer 50, the second image acquirer 60, the position determiner 70, and the medical image processing device 100 constituting the medical device are shown in FIG. 2. Also, the connection relationship between the comparative image database 110 and the bed controller 11 related to the medical device including the medical image processing device 100 is also shown in FIG. 2. Also, because the connection relationship between the display controller 80 constituting the medical device and other components (more specifically, the medical image processing device 100) in FIG. 2 can be easily understood from FIG. 1, a description thereof will be omitted.

A comparative image collected in the comparative image database 110 is a set of a segment image and a valid region image. In FIG. 2, a state in which a plurality of comparative images Ci including comparative images Ci-1 to Ci-n are collected in the comparative image database 110 is shown. Also, in FIG. 2, a set of a segment image Di-1 and a valid region image Ei-1 constitutes the comparative image Ci-1, a set of a segment image Di-2 and a valid region image Ei-2 constitutes the comparative image Ci-2, and a set of a segment image Di-n and a valid region image Ei-n constitutes a comparative image Ci-n. Also, a hyphen "-" indicated after a reference sign of the comparative image Ci and a number subsequent to the hyphen are used for identifying a corresponding relationship. In the following description, when images are represented without being distinguished, they are represented without the hyphen "-" and the number subsequent to the hyphen.

The segment image is a segment patch image obtained by cutting out a range of a prescribed size from one three-dimensional volume image (for example, a CT image) used in position alignment of the patient in the previous radiation treatment. A region of interest where attention is paid to alignment of the position of the patient in the radiation treatment at that time (the patient is in a direction in which the treatment beam B is radiated to the treatment portion) is included in the CT image used in position alignment of the patient in the previous radiation treatment and the like. This region of interest is a proven region used to align the position of the patient in the previous radiation treatment. The segment image is an image obtained by cutting out a prescribed range including a characteristic shape of the region of interest. Here, the region of interest is, for example, a region where an image of a bone within the patient's body is shown as a region designated as, for example, a region of interest when the radiation treatment practitioner (the doctor or the like) aligns the position of the patient in the previous radiation treatment. The region of interest included in the segment image is not limited to the region designated for the patient P of a treatment target at present. For example, the region of interest included in the segment image may be a region designated in previous radiation treatment by, for example, the radiation treatment practitioner (the doctor or the like) to align the position of the patient at that time. In other words, the region of interest included in the segment image is a region designated for performing radiation treatment at the same treatment portion, but is a region designated for a plurality of unspecified patients.

The valid region image is an image in which a region of interest capable of being validly used when the position of the patient is aligned in the radiation treatment to be performed among regions of interest included in the corresponding segment image is shown as a valid region. Thus, in the valid region image, for example, only some regions of interest among the regions of interest designated by the radiation treatment practitioner (the doctor or the like) in the previous radiation treatment may be shown as valid regions.

Figure 3:
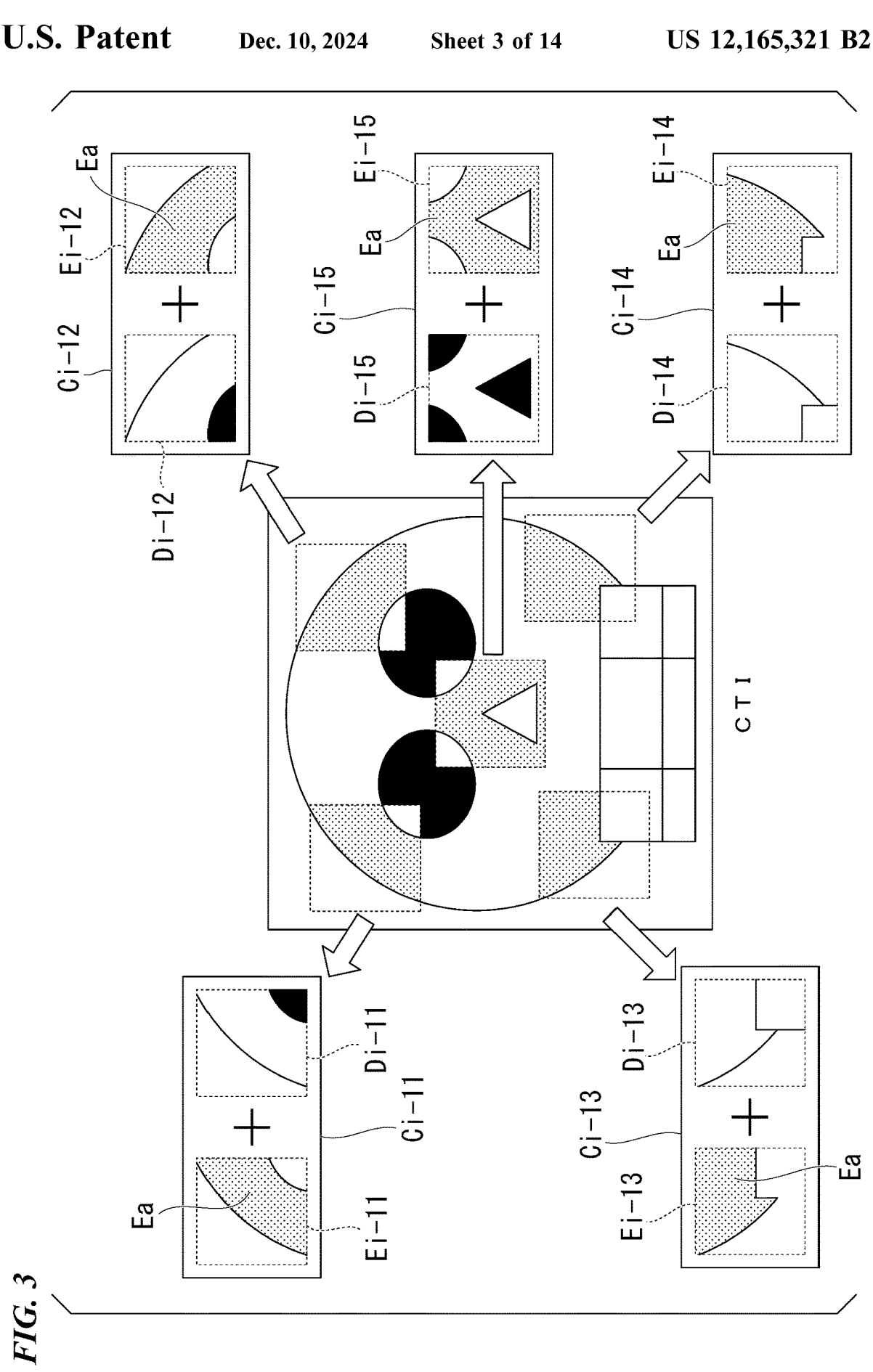
FIG. 3 is a diagram showing an example of a comparative image referred to by the medical image processing device of the first embodiment.

Here, an example of the comparative image Ci collected in the comparative image database 110 will be described. FIG. 3 is a diagram showing an example of a comparative image Ci referred to by the medical image processing device 100 of the first embodiment. An example of a comparative image Ci corresponding to a disease having a treatment portion to be irradiated with the treatment beam B within a range of the patient P's face is shown in FIG. 3. A CT image CTI shown in FIG. 3 is an image diagram of a bone (a skull) of the patient's head.

In the example of the comparative image Ci shown in FIG. 3, five segment images (segment images Di-11 to Di-15) and five valid region images (valid region images Ei-11 to Ei-15) corresponding to the bones (the skull (the image diagram)) of the patient's head are paired. Although the comparative image Ci collected in the comparative image database 110 may be a three-dimensional image or a two-dimensional image as described above, an example of a two-dimensional comparative image Ci is shown for ease of description in FIG. 3.

As described above, each segment image Di is an image obtained by cutting out a region of interest including a characteristic shape from one three-dimensional volume image (for example, a CT image CTI) used for the position alignment of the patient in previous radiation treatment in a prescribed range. In FIG. 3, an example of the segment image Di including a curved portion of the outer circumference of the skull or a portion of the eye or the nose as the characteristic shape is shown. Also, as described above, in each valid region image Ei, a characteristic shape included in the corresponding segment image Di is shown as a valid region capable of being validly used when the position alignment of the patient is performed in the radiation treatment. In FIG. 3, an example of the valid region image Ei in which a bone portion of the skull is the valid region Ea is shown. Also, the valid region Ea in the valid region image Ei is not limited to the bone portion as shown in FIG. 3, and, for example, a shape of the boundary between a portion where there is a bone and a portion where there is no bone (a shape of a boundary portion between the bone of the skull and the curve of the outer circumference, the eyes, or the nose in FIG. 3) may be used as the valid region. As described above, the comparative image Ci collected in the medical image processing device 100 is a set of images in which the segment image Di and the valid region image Ei are paired. Thus, the segment image Di and the valid region image Ei may be assigned the same information (for example, the same identification information (ID)) to indicate that they are a set.

Also, as described above, the valid region Ea shown in the valid region image Ei may be only a part of the region of interest included in the segment image Di. In the example shown in FIG. 3, for example, the valid region image Ei-13 and the valid region image Ei-14 are examples of the valid region image Ei in which only a part of the region of interest included in the segment image Di is shown as the valid region Ea. In the valid region image Ei-13 and the valid region image Ei-14, the bone of a jaw portion is excluded from the valid region Ea. This is because the jaw portion of the patient includes a joint part whose shape changes according to how the patient's mouth is opened at the time of photography and is not considered to be necessarily a valid part for the position alignment of the patient. Also, for example, in the case where the bone of the joint part is also considered to be a valid region such as the case of a disease in which the treatment portion of the radiation treatment moves together with the bone, the bone of the joint part may also be used as a valid region in the valid region image Ei. For this reason, as described above, the comparative image Ci differs in configurations of segment images Di and valid region images Ei collected for each treatment portion and the number thereof. Also, for example, the segment image Di may show a fixing jig for fixing the patient. In this case, in the valid region image Ei, the fixing jig is excluded from the valid region regardless of a difference in the treatment portion. This is because the fixing jig is a jig for fixing the posture of the current patient and it is more appropriate to think that the posture of the current patient cannot be fixed to be the same as the posture at the time of the previous radiation treatment.

Figure 4:
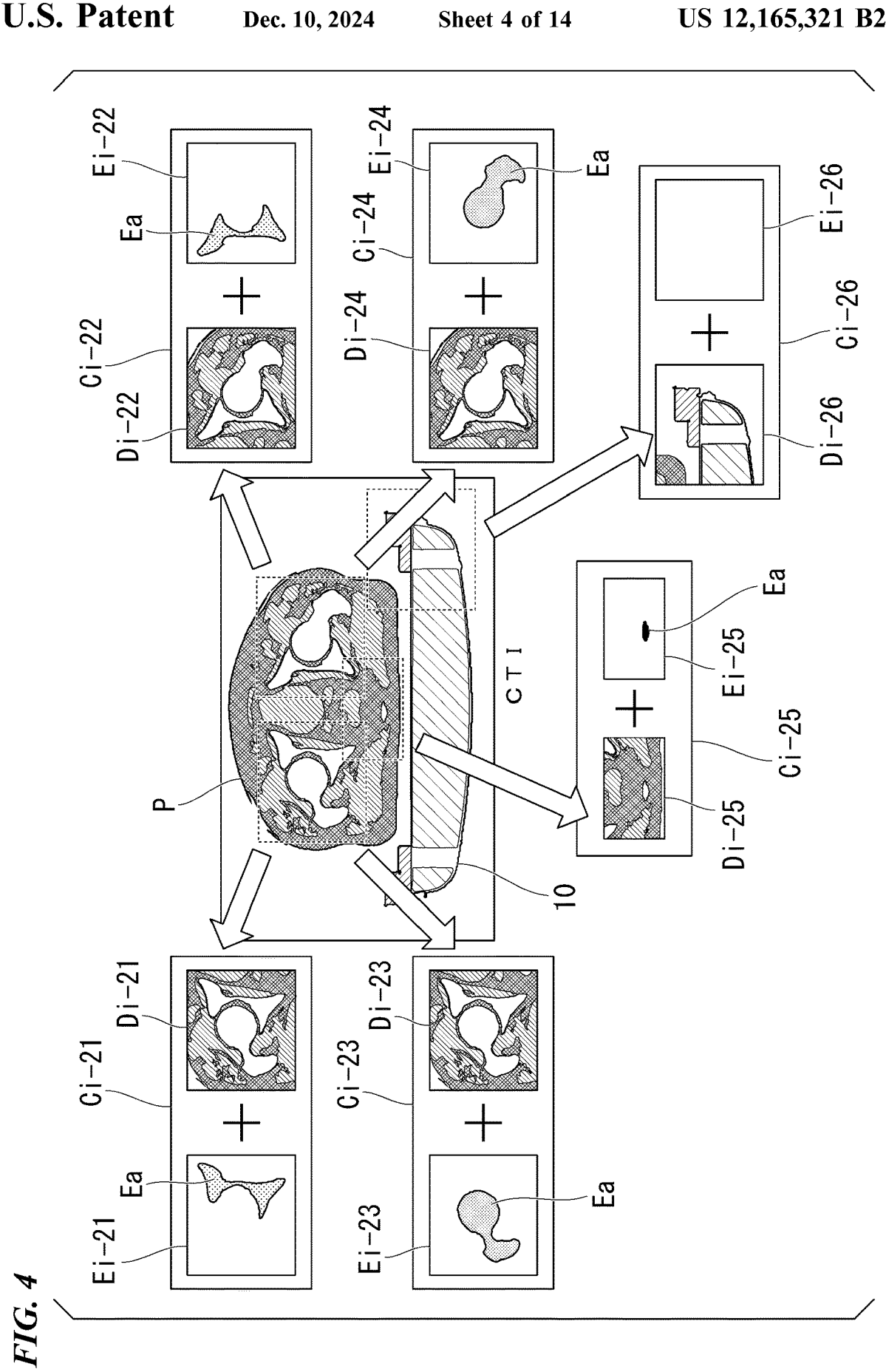
FIG. 4 is a diagram showing another example of a comparative image referred to by the medical image processing device of the first embodiment.

As described above, in the comparative image database 110, a set of a segment image Di obtained by cutting out the region of interest including the characteristic shape from one three-dimensional volume image used for the position alignment of the patient in the previous radiation treatment in a prescribed range and a valid region image Ei corresponding to the segment image Di is collected together for each treatment portion. FIG. 4 is a diagram showing another example of the comparative image referred to by the medical image processing device of the first embodiment. An example of a comparative image Ci corresponding to a disease in which there is a treatment portion that is irradiated with the treatment beam B within a range of the patient's waist is shown in FIG. 4. Also, in the CT image CTI shown in FIG. 4, the background color is white so that a subject is more easily recognized.

In the example of the comparative image Ci shown in FIG. 4, two segment images (a segment image Di-21 and a segment image Di-22) and two valid region images (a valid region image Ei-21 and a valid region image Ei-22) corresponding to the bones of the patient's pelvis are paired. Also, in the example of the comparative image Ci shown in FIG. 4, two segment images (a segment image Di-23 and a segment image Di-24) and two valid region images (a valid region image Ei-23 and a valid region image Ei-24) corresponding to the bones of the patient's foot are paired. Also, in the example of the comparative image Ci shown in FIG. 4, one segment image Di-25 and one valid region image Ei-25 corresponding to the patient's coccyx are paired. Also, in FIG. 4, as an example of a comparative image Ci of a part other than the patient's body, one segment image Di-26 and one valid region image Ei-26 corresponding to a structural part of the treatment table 10 are paired. Also, in FIG. 4, an example of a two-dimensional comparative image Ci is shown for ease of description.

In the example shown in FIG. 4, the segment image Di-21 and the segment image Di-23 are the same segment image Di. Also, in the example shown in FIG. 4, the segment image Di-22 and the segment image Di-24 are the same segment image Di. However, a different valid region Ea is shown in each corresponding valid region image Ei. This is to select the valid region image Ei in accordance with various conditions such as a difference in the treatment portion due to radiation treatment and whether or not a joint portion whose shape changes as described above is included. The valid region image Ei-21 and the valid region image Ei-23 respectively corresponding to the segment image Di-21 and the segment image Di-23 shown in FIG. 4 are generated as valid region images Ei that differ in accordance with a difference of whether the valid region Ea is the bone of the pelvis or the foot. Likewise, both the valid region image Ei-22 and the valid region image Ei-24 respectively corresponding to the segment image Di-22 and the segment image Di-24 shown in FIG. 4 are generated as valid region images Ei that differ in accordance with a difference of whether the valid region Ea is the bone of the pelvis or the foot. This is because the relationship between positions or angles of the bones of the pelvis and the foot is not always the same according to the posture of the patient during treatment, the posture of the patient during photography, or the like.

The set of the segment image Di-25 and the valid region image Ei-25 corresponding to the patient's coccyx shown in FIG. 4 can be used at the same time, in, for example, either case where the valid region Ea is a pelvic bone or a foot bone.

Also, an example of a case where a part of the treatment table 10 is included in the segment image Di-26 is shown as an example of a structural part other than the patient's body excluded from the valid region Ea in FIG. 4. As described above, a part other than the patient's body is excluded from the valid region Ea regardless of a difference in the treatment portion. Thus, the valid region Ea is not shown in the valid region image Ei-26 corresponding to the segment image Di-26. In this way, even if the part excluded from the valid region is shown in the segment image Di, a region that is not used when the position of the patient is aligned (in other words, an invalid region) can be excluded in a state in which the unused region is not shown as the valid region Ea in the valid region image Ei.

Returning to FIG. 2, the medical image processing device 100 includes a comparator 101 and a position determination region determiner 102.

The comparator 101 compares a three-dimensional volume image (for example, a CT image) output by the first image acquirer 50 with each comparative image Ci (more specifically, a segment image Di) collected in the comparative image database 110. At this time, the comparator 101 selects an image group of comparative images Ci corresponding to the treatment portion and compares the segment image Di included in the selected image group with the CT image. For information for selecting the image group of the comparative image Ci to be compared by the comparator 101, for example, the radiation treatment practitioner (the doctor or the like) may operate the user interface such as the operator (not shown) and input information of the treatment portion or the CT image may include information of the treatment portion. The comparator 101 compares the CT image with the comparative image Ci by, for example, calculating a square error of luminance in pixels constituting the image of each of the CT image and the comparative image Ci. A method of comparing the CT image with the comparative image Ci in the comparator 101 is not limited to a method of calculating the square error. As a result of comparing the CT image with the comparative image Ci, the comparator 101 selects the segment image Di similar to that at any position in the CT image (for example, the segment image Di whose degree of similarity to the CT image is greater than or equal to a prescribed value). The comparator 101 outputs information indicating a comparison result to the position determination region determiner 102. The comparator 101 may output information indicating the selected segment image Di (for example, identification information (ID) assigned to the segment image Di) and information of a position within the CT image similar to the segment image Di as information of a comparison result to the position determination region determiner 102. Also, the comparator 101 may include information of the degree of similarity between the CT image and the segment image Di in the information of the comparison result and output the information to the position determination region determiner 102. When there are a plurality of segment images Di similar to the CT image, the comparator 101 outputs information of a comparison result corresponding to each segment image Di to the position determination region determiner 102.

The position determination region determiner 102 determines a range of the valid region included within the CT image as a position determination region on the basis of the information of the comparison result output by the comparator 101. The position determination region determiner 102 determines a range of the valid region Ea included within the CT image as the position determination region by extracting the valid region Ea shown in the valid region image Ei corresponding to the segment image Di selected by the comparator 101 and allocating the extracted valid region Ea to the inside of the CT image. Also, when the information of the comparison result output by the comparator 101 indicates that there is a similarity in the plurality of segment images Di, the position determination region determiner 102 combines ranges of valid regions Ea shown in valid region images Ei corresponding to segment images Di and determines a range obtained by combining the ranges of the valid regions Ea as a range of a position determination region in the CT image. At this time, if there is an overlapping range in the valid region Ea shown in each valid region image Ei, the position determination region determiner 102 may determine a position determination region using only the valid region Ea shown in any one valid region image Ei. Also, the position determination region determiner 102 may determine the position determination region by averaging ranges of overlapping valid regions Ea. Also, the position determination region determiner 102 may determine the position determination region by performing a weighted averaging process on the ranges of the overlapping valid region Ea on the basis of the information of the degree of similarity included in the information of the comparison result output by the comparator 101. Also, the position determination region determiner 102 may determine the position determination region by employing a mode value of the range of each overlapping valid region Ea. The position determination region determiner 102 outputs information indicating the range of the position determination region within the determined CT image to the position determiner 70. Also, the position determination region determiner 102 outputs the CT image and the position determination region within the determined CT image to the display controller 80.

According to such a configuration, in the medical image processing device 100, the comparator 101 compares the CT image with the segment image Di and the position determination region determiner 102 determines the position determination region within the CT image. Thereby, in the medical image processing device 100, for example, it is possible to automatically set a position determination region similar to a region of interest used in position alignment of patients subjected to the treatment of the same treatment portion in the previous radiation treatment without designating a region of interest when the radiation treatment practitioner (the doctor or the like) operates the user interface such as the operator (not shown) to align the position of the patient P. Thereby, in the medical device including the medical image processing device 100, the direction of the patient P to be treated in the radiation treatment can be directed to the position determined by the position determiner 70, i.e., the patient P can be directed in a direction suitable for radiating the treatment beam B.

Figure 5:
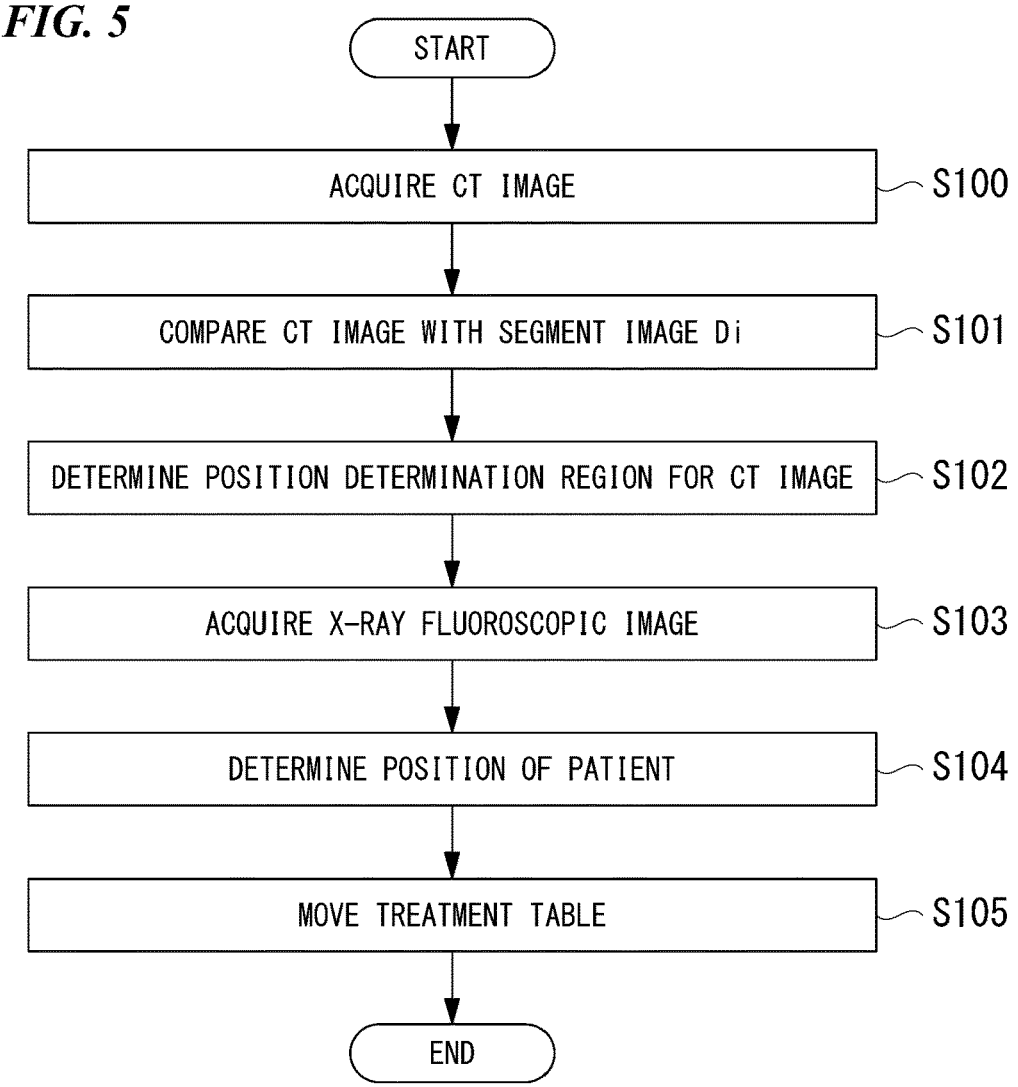
FIG. 5 is a flowchart showing a flow of an operation in the treatment system of the first embodiment.

Next, an operation of the treatment system 1 will be schematically described. FIG. 5 is a flowchart showing a flow of an operation in the treatment system 1 of the first embodiment. In the following description, it is assumed that the patient P is photographed by the CT device in advance and a CT image (a three-dimensional volume image) is provided. Also, it is assumed that information of the treatment portion of the patient P who will be subjected to radiation treatment from now on is input to the treatment system 1. That is, it is assumed that the medical image processing device 100 (more specifically, the comparator 101) has already input which image group of the comparative images Ci collected in the comparative image database 110 is to be selected.

When the treatment system 1 starts an operation, the first image acquirer 50 acquires a CT image (step S100). The first image acquirer 50 outputs the acquired CT image to the position determiner 70 and the comparator 101 provided in the medical image processing device 100.

Subsequently, the comparator 101 compares the CT image output by the first image acquirer 50 with a segment image Di of each treatment portion collected in the comparative image database 110 (step S101). The comparator 101 outputs information of a comparison result to the position determination region determiner 102.

Subsequently, the position determination region determiner 102 determines a position determination region for the CT image on the basis of the information of the comparison result output by the comparator 101 (step S102). The position determination region determiner 102 outputs information indicating a range of the position determination region determined for the CT image to the position determiner 70.

Figure 6A:
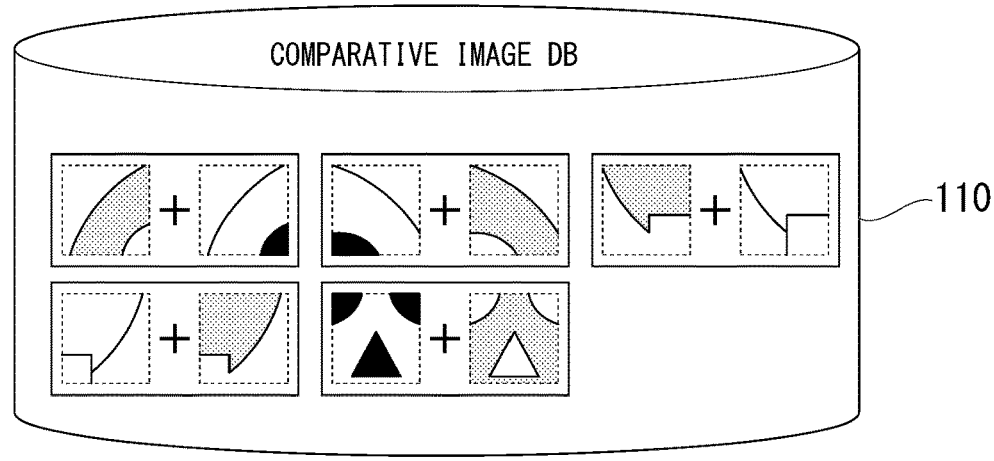
FIG. 6A is a diagram schematically showing an example of operations of the comparator and a position determination region determiner provided in the medical image processing device of the first embodiment.
Figure 6B:
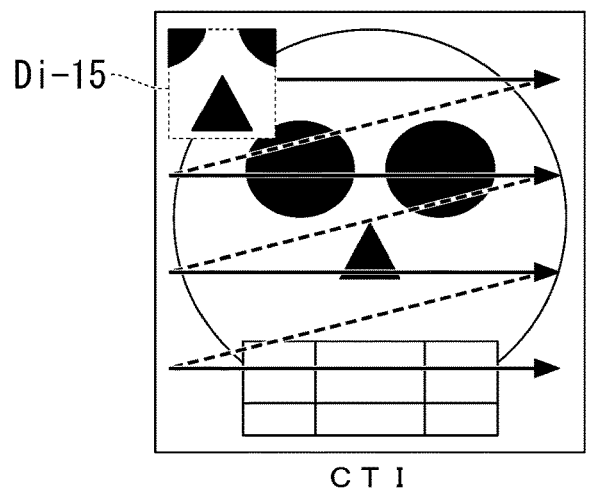
FIG. 6B is a diagram schematically showing an example of operations of the comparator and the position determination region determiner provided in the medical image processing device of the first embodiment.
Figure 6C:
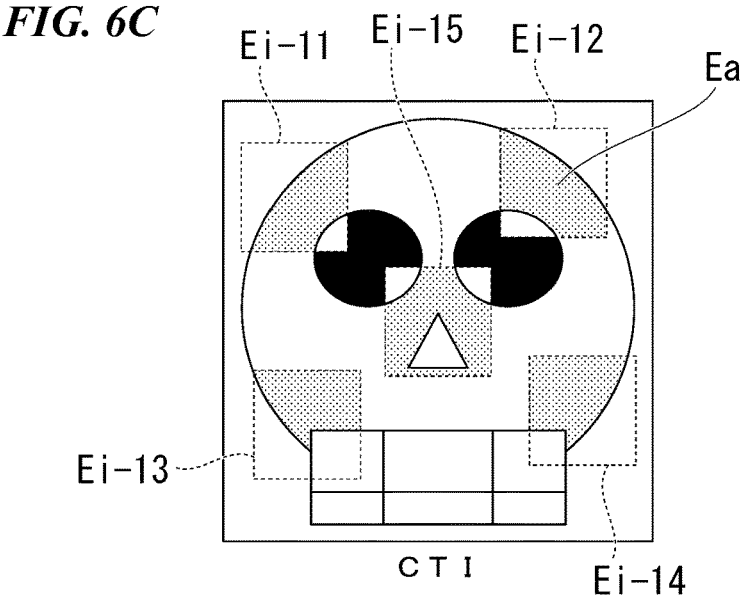
FIG. 6C is a diagram schematically showing an example of operations of the comparator and the position determination region determiner provided in the medical image processing device of the first embodiment.
Figure 6D:
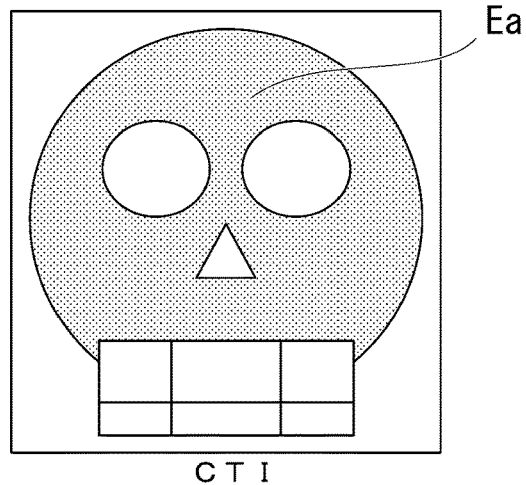
FIG. 6D is a diagram schematically showing an example of operations of the comparator and the position determination region determiner provided in the medical image processing device of the first embodiment.

Here, an operation example of a process of comparison between the CT image and the segment image Di in the comparator 101 (step S101) and determination of the position determination region for the CT image in the position determination region determiner 102 (step S102) will be described. FIGS. 6A, 6B, 6C, and 6D are diagrams schematically showing examples of operations of the comparator 101 and the position determination region determiner 102 provided in the medical image processing device 100 of the first embodiment. A state in which comparative images Ci are collected in the comparative image database 110 is shown in FIG. 6A. Also, an operation example of comparison between a CT image CTI and a segment image Di in the comparator 101 is schematically shown in FIG. 6B. Also, an example of an operation of determination of the position determination region for the CT image CTI (allocation of the valid region to the CT image CTI) in the position determination region determiner 102 is schematically shown in FIGS. 6C and 6D. In the following description, as shown in FIG. 6A, it is assumed that the comparative image Ci corresponding to the bone (the skull (the image diagram)) of the patient's head as shown in FIG. 3 is collected in the comparative image database 110.

In step S101, the comparator 101 first selects an image group of the comparative images Ci collected in the comparative image database 110. The comparator 101 searches for a position similar to that of each segment image Di included in the selected image group within the CT image CTI output by the first image acquirer 50. In the search for the position similar to that of the segment image Di in the comparator 101, the degree of similarity between the segment image Di and the CT image CTI is obtained at each position while the segment image Di is sequentially moved within the CT image CTI and a position where the obtained degree of similarity is greater than or equal to a prescribed value is set as a position within the CT image CTI similar to the segment image Di. In the operation example shown in FIG. 6B, a state in which the position within the CT image CTI similar to the segment image Di-15 is searched for by sequentially moving the segment image Di-15 so that a scan (raster scan) process is performed on the segment image Di-15 within the CT image CTI and obtaining the degree of similarity between the segment image Di-15 and the CT image CTI at each position is shown. The comparator 101 searches for a position similar to that of the segment image Di with respect to all the segment images Di included in the selected image group, associates information indicating a segment image Di in which the similar position within the CT image CTI is obtained (in which there is a position where the degree of similarity is greater than or equal to a prescribed value) with information of the obtained position within the CT image CTI, and outputs an association result as information of a comparison result to the position determination region determiner 102.

Also, a method in which the comparator 101 compares the CT image CTI with the segment image Di in step S101 is not limited to a method of obtaining the degree of similarity while the selected segment image Di is sequentially moved within the CT image CTI as shown in FIG. 6B. For example, the method may be a method of sequentially cutting out a range of a size that is the same as a size of the segment image Di from the CT image CTI to perform a raster scan process and comparing an image of the cut-out range with each segment image Di included in the selected image group. In other words, the method may be a method of searching for a segment image Di at a position similar to a prescribed position within the CT image CTI in contrast with the operation example shown in FIG. 6B for searching for the position within the CT image CTI similar to the segment image Di.

Subsequently, in step S102, the position determination region determiner 102 first selects and acquires the valid region image Ei corresponding to the segment image Di shown in the information of the comparison result output by the comparator 101 from the image group of the comparative images Ci collected in the comparative image database 110. The position determination region determiner 102 extracts a valid region shown in each acquired valid region image H and allocates the extracted valid region to the inside of the CT image CTI. In the operation example shown in FIG. 6C, a state in which the valid region images Ei-11 to Ei-15 respectively corresponding to the segment images Di-11 to Di-15 shown in the information of the comparison result output by the comparator 101 are acquired and the valid region Ea shown in each valid region image Ei is allocated to the inside of the CT image CTI is shown. The position determination region determiner 102 determines the range of the valid region Ea allocated to the inside of the CT image CTI as described above as the position determination region and outputs information indicating a range of the determined position determination region to the position determiner 70.

Although the case where the five comparative images Ci corresponding to the bones (the skull (the image diagram)) of the patient's head are collected in the comparative image database 110 in FIG. 3, FIG. 6A, FIG. 6B, FIG. 6C, and FIG. 6D is shown, a comparative image Ci representing a valid region designated as a region of interest by, for example, the radiation treatment practitioner (the doctor or the like) when the position of the patient is aligned in the previous radiation treatment is collected in the comparative image database 110 as described above. Thus, for example, according to a case where the number of comparative images Ci collected in the comparative image database 110 increases or the like, there is a possibility that the valid region Ea will be allocated to the entire skull of the patient P shown within the CT image CTI as shown in FIG. 6D. In this case, the position determination region determiner 102 determines the entire range of the skull of the patient P shown within the CT image CTI as the position determination region and outputs information indicating that the entire range of the skull is the range of the position determination region to the position determiner 70.

Returning to FIG. 5, the second image acquirer 60 subsequently acquires an X-ray fluoroscopic image PT of the inside of the body of the current patient P output by each radiation detector 30 (step S103). The second image acquirer 60 outputs the acquired X-ray fluoroscopic image PI to the position determiner 70.

Subsequently, the position determiner 70 collates the CT image output by the first image acquirer 50 with the X-ray fluoroscopic image PI output by the second image acquirer 60 on the basis of the information indicating the range of the position determination region output by the position determination region determiner 102 and determines the position of the patient P (step S104). Further, the position determiner 70 obtains an amount of movement for moving the treatment table 10 to the determined position of the patient P. The position determiner 70 outputs information of the obtained amount of movement of the treatment table 10 to the bed controller 11.

Subsequently, the bed controller 11 causes the treatment table 10 to be moved on the basis of the information of the amount of movement output by the position determiner 70 (step S105). Thereby, the current position of the patient P fixed on the treatment table 10 is moved to a position suitable for performing radiation treatment.

As described above, the medical image processing device 100 determines a position determination region for use in the position alignment of the patient P with respect to the CT image output by the first image acquirer 50 with reference to the comparative image Ci collected in the comparative image database 110 and outputs information indicating a range of the determined position determination region to the position determiner 70. More specifically, in the medical image processing device 100, the comparator 101 compares the CT image output by the first image acquirer 50 with the segment image Di constituting the comparative image Ci collected in the comparative image database 110. In the medical image processing device 100, the position determination region determiner 102 allocates the valid region Ea indicated by the valid region image Ei constituting the comparative image Ci to the inside of the CT image on the basis of the information of the comparison result output by the comparator 101, determines a position determination region for use in the position alignment of the patient P, and outputs information indicating the range of the determined position determination region to the position determiner 70. Thereby, in the treatment system 1 provided with the medical device including the medical image processing device 100, for example, it is possible to automatically set the position determination region at the treatment stage for performing the radiation treatment in a state in which the radiation treatment practitioner (the doctor or the like) does not designate the position determination region even if a position determination region for use in position alignment of the patient P in the CT image captured at the planning stage of radiation treatment is not determined. In other words, in the treatment system 1 provided with the medical device including the medical image processing device 100, it is possible to automatically set a proven position determination region used when the position alignment of the patient is performed in the previous radiation treatment.

Also, in the medical device including the medical image processing device 100, the position determiner 70 collates a CT image output by the first image acquirer 50 with the X-ray fluoroscopic image PI output by the second image acquirer 60 on the basis of the information indicating the range of the position determination region output by the position determination region determiner 102 and determines the position of the patient P. The position determiner 70 obtains the amount of movement of the treatment table 10 on the basis of the determined position of the patient P and outputs information of the obtained amount of movement of the treatment table 10 to the bed controller 11. Thereby, in the treatment system 1 provided with the medical device including the medical image processing device 100, the current position of the patient P fixed on the treatment table 10 can be moved to a position suitable for performing radiation treatment. As described above, in the treatment system 1 provided with the medical device including the medical image processing device 100, the position determination for the patient P in the radiation treatment can be performed with high accuracy.

Also, in the above description, the case where the comparative image Ci collected in the comparative image database 110 is a segment patch image obtained by cutting out a range of a prescribed size from one three-dimensional volume image (for example, CT image) used for the position alignment of the patient in the previous radiation treatment has been described. In other words, the case where the segment image Di is a three-dimensional patch image has been described. However, the segment image Di is not limited to the three-dimensional patch image. For example, the segment image Di may be a two-dimensional patch image obtained by cutting out the entire range of a prescribed angle from one three-dimensional volume image or one two-dimensional image itself. In this case, the comparator 101 may similarly select a two-dimensional segment image Di whose degree of similarity to the CT image is greater than or equal to a prescribed value and output information indicating the selected two-dimensional segment image Di (for example, identification information (ID) assigned to the segment image Di) as information of a comparison result to the position determination region determiner 102. Also, the comparator 101 may select one two-dimensional segment image Di having the highest degree of similarity and output identification information (ID), assigned to the one two-dimensional segment image Di having the highest degree of similarity that has been selected, as the information of the comparison result to the position determination region determiner 102. In this case, the position determination region determiner 102 may output the range of the valid region Ea shown in the two-dimensional valid region image Ei corresponding to the two-dimensional segment image Di selected by the comparator 101 as information indicating the range of the position determination region within the determined CT image to the position determiner 70 as itis.

Also, in the treatment system 1, because the positions of the radiation source 20 and the radiation detector 30 are fixed, a photography direction in which the photography device including the set of the radiation source 20 and the radiation detector 30 (the relative direction for the fixed coordinate system in the treatment room) is fixed. However, in the treatment system 1, as shown in FIG. 1, the X-ray fluoroscopic image PI of the patient P is captured from two different directions. That is, the X-ray fluoroscopic image PI of the patient P photographed in the treatment system 1 is a three-dimensional image. Thus, the collation between the CT image and the X-ray fluoroscopic image PI performed by the position determiner 70 to determine the position of the patient P becomes the collation between the three-dimensional images. In this case, the position determiner 70 determines a position where an error between the CT image and the X-ray fluoroscopic image PI is minimized as a position of the patient P suitable for performing radiation treatment by, for example, moving the CT image with translation and rotation parameters. At this time, the position determiner 70 may change a weight value of the error between the valid region Ea and a region other than the valid region Ea within the CT image on the basis of the information indicating the range of the position determination region output by the position determination region determiner 102 and use the valid region Ea to determine the position of the patient P. Also, the position determiner 70 may determine the position of the patient P suitable for performing radiation treatment using the amount of mutual information of each of the CT image and the X-ray fluoroscopic image PI.

Also, as described above, in the treatment system 1, the case where the images which are collated when the position determiner 70 determines the position of the patient P are the CT image and the X-ray fluoroscopic image PI, i.e., images captured by different photography devices (modalities), has been described. However, a case where the images which are collated when the position determiner 70 determines the position of the patient P are images captured by the same photography device (modality) is also conceivable. In this case, the position determiner 70 may determine a position where an error between images is minimized using the sum of squares of residuals, the sum of absolute values of residuals, a normalized intercorrelation, and the like associated with the pixels constituting each image as the position of the patient P suitable for performing radiation treatment.

Also, as described above, in the treatment system 1, the case where the position determiner 70 determines the position of the patient P by collating the three-dimensional images of the CT image and the X-ray fluoroscopic image PI with each other has been described. However, a case where the images which are collated when the position determiner 70 determines the position of the patient P are images of different dimensions is also conceivable. For example, when the number of sets of radiation sources 20 and radiation detectors 30 is one in the treatment system 1, the X-ray fluoroscopic image PI becomes a two-dimensional image. In this case, when the error between the CT image and the X-ray fluoroscopic image PI is calculated, the position determiner 70 may perform the collation between two-dimensional images by projecting the CT image onto the two-dimensional image in accordance with geometry information of the X-ray fluoroscopic image PI. In this case, likewise, the position determiner 70 also projects the range of the position determination region (i.e., the range of the valid region Ea) output by the position determination region determiner 102 onto the two-dimensional image in accordance with the geometry information. Thereby, as in the case where the three-dimensional images described above are collated, the position determiner 70 can change a weight value of an error between the valid region Ea within the CT image and a region other than the valid region Ea and use the valid region Ea to determine the position of the patient P. At this time, the position determiner 70 also uses a similarity scale when the CT image projected onto the two-dimensional image is collated with the two-dimensional X-ray fluoroscopic image PI similar to a similarity scale when the three-dimensional images described above are collated. The "geometry information" is information capable of indicating the positions of the radiation source 20 and the radiation detector 30 using three-axial coordinate values when three-dimensional coordinates are defined within a three-dimensional space where the treatment system 1 is installed. By using this geometry information, it is possible to obtain the position of the patient P located at any position within prescribed three-dimensional coordinates from a position where radiation r radiated from the radiation source 20 passes through the body of the patient P and arrives at the radiation detector 30. Also, the geometry information can be obtained from installation positions of the radiation source 20 and the radiation detector 30 designed when the treatment system 1 is installed. Also, the geometry information can be obtained from the installation positions of the radiation source 20 and the radiation detector 30 measured by a three-dimensional measurement instrument or the like.

The position determiner 70 determines the position of the patient P suitable for performing radiation treatment by moving the CT image and aligning the position of the CT image with the position of the X-ray fluoroscopic image PI. However, in actual radiation treatment, the treatment beam B is radiated to the treatment portion of the patient P from an irradiation direction predetermined with respect to the CT image at the planning stage of the radiation treatment. Thus, the amount of movement of the treatment table 10 obtained by the position determiner 70 is obtained through an inverse calculation operation from the amount of movement and the direction of the CT image moved so that the position of the CT image is aligned with the position of the X-ray fluoroscopic image PI. In other words, the amount of movement of the treatment table 10 obtained by the position determiner 70 is an amount of movement required to move the patient P fixed on the treatment table 10 so that each radiation detector 30 can capture an X-ray fluoroscopic image PI that is the same as the CT image captured at the planning stage.

As described above, the medical image processing device 100 includes the comparator 101 configured to compare a first image (a three-dimensional volume image (for example, a CT image)) obtained by photographing the patient P with a comparative image Ci which is an image (a three-dimensional volume image (for example, a CT image)) used in previous radiation treatment and in which a valid region Ea used in position alignment in the radiation treatment is designated; and the position determination region determiner 102 configured to determine a position determination region similar to the valid region Ea included within the first image on the basis of a comparison result of the comparator 101.

As described above, in the medical image processing device 100, a plurality of comparative images Ci may be collected in the previous radiation treatment, the comparative image Ci may include a valid region image in which a part of each of segment images Di into which one fluoroscopic image PI (a three-dimensional volume image (for example, a CT image)) used in the previous radiation treatment is segmented in a prescribed size is designated as the valid region Ea, and the position determination region determiner 102 may determine the position determination region by extracting locations similar to the valid region Ea within the first image with respect to the plurality of comparative images Ci and combining the locations extracted with respect to the plurality of comparative images Ci.

Also, as described above, in the medical image processing device 100, a plurality of comparative images Ci may be provided, the comparative images Ci may be grouped into a plurality of image groups for each treatment portion treated in the previous radiation treatment, and the comparator 101 may select an image group of the comparative images Ci to be compared with the first image in accordance with the treatment portion of the patient P.

Also, as described above, in the medical image processing device 100, the first image may be a DRR image.

Also, as described above, a medical device may include the first image acquirer 50 configured to acquire the first image (a three-dimensional volume image (for example, a CT image)) by photographing the patient P; the second image acquirer 60 configured to acquire a second image (an X-ray fluoroscopic image PI) according to the radiation r with which the patient P is irradiated at a time point different from a photography time point of the first image from a photography device that performs a process of detecting the radiation r that has been radiated using the radiation detector 30 and imaging the detected radiation r; the medical image processing device 100, and the position determiner 70 configured to determine the position of the patient P when the radiation treatment is performed on the basis of the position determination region using the first image and the X-ray fluoroscopic image PI.

Also, as described above, the medical device may further include the display controller 80 configured to cause the display device 81 to display an image obtained by superimposing the position determination region on the first image.

Also, as described above, the treatment system 1 may include: the medical device; the treatment beam irradiation gate 40 configured to radiate a treatment beam B to a treatment portion of the patient P; and the bed controller 11 configured to control an amount of movement of a position of the treatment table 10 on which the patient P is fixed in alignment with a position determined by the position determiner 70.

Also, the medical image processing device 100 is implemented by a processor such as a CPU and a GPU, hardware such as an LSI circuit, an ASIC, or an FPGA, a dedicated LSI circuit, or the like, and includes a storage device such as a ROM, a RAM, an HDD, or a flash memory. There may be provided a device having the storage device storing a medical image processing program for causing the processor to function as the medical image processing device 100 including the comparator 101 configured to compare a first image (a three-dimensional volume image (for example, a CT image)) obtained by photographing the patient P with a comparative image Ci which is an image (a three-dimensional volume image (for example, a CT image)) used in previous radiation treatment and in which a valid region Ea used in position alignment in the radiation treatment is designated; and the position determination region determiner 102 configured to determine a position determination region similar to the valid region Ea included within the first image on the basis of a comparison result of the comparator 101.

Second Embodiment

Hereinafter, a second embodiment will be described. Also, a configuration of a treatment system provided with a medical device including a medical image processing device of the second embodiment is a configuration obtained by replacing the medical image processing device 100 with the medical image processing device of the second embodiment (hereinafter, referred to as a "medical image processing device 200") in the configuration of the treatment system 1 provided with the medical device including the medical image processing device 100 of the first embodiment shown in FIG. 1. In the following description, a treatment system provided with a medical device including the medical image processing device 200 is referred to as a "treatment system 2."

Also, in the following description, components similar to those of the treatment system 1 provided with the medical device including the medical image processing device 100 of the first embodiment among components of the treatment system 2 provided with the medical device including the medical image processing device 200 are denoted by the same reference signs and a detailed description of the similar components will be omitted. In the following description, only the configurations, operations, and processes of the medical image processing device 200, which is a component different from the medical image processing device 100 of the first embodiment, will be described.

In the treatment system 2, a combination of a first image acquirer 50, a second image acquirer 60, a position determiner 70, a display controller 80, and a medical image processing device 200 is an example of a "medical device" in the claims. Also, for example, a hardware processor such as a CPU and a storage device (a storage device including a non-transitory storage medium) storing a program (software) are provided for some or all of the functions of the components provided in the medical device and the functions of the components may be implemented by the processor executing the program. Also, some or all of the functions of the components provided in the medical device may be implemented by hardware (including a circuit unit; circuitry) such as an LSI circuit, an ASIC, an FPGA, or a GPU or the functions of the components may be implemented by software and hardware in cooperation. Also, some or all of the functions of the components provided in the medical device may be implemented by a dedicated LSI circuit. Here, the program (software) may be pre-stored in a storage device (a storage device including a non-transitory storage medium) provided in the treatment system 2 such as a ROM, a RAM, an HDD, or a flash memory or may be stored in a removable storage medium (a non-transitory storage medium) such as a DVD or a CD-ROM and installed in the storage device provided in the treatment system 2 when the storage medium is mounted in a drive device provided in the treatment system 2. Also, the program (software) may be downloaded in advance from another computer device via the network and installed in the storage device provided in the treatment system 2.

Like the medical image processing device 100 of the first embodiment, the medical image processing device 200 determines a position determination region for use in position alignment of a patient P with respect to a CT image output by the first image acquirer 50 with reference to a comparative image collected in a comparative image database 110. Like the medical image processing device 100 of the first embodiment, the medical image processing device 200 outputs information of the determined position determination region to the position determiner 70. Also, like the medical image processing device 100 of the first embodiment, the medical image processing device 200 outputs the CT image output by the first image acquirer 50 and the information of the determined position determination region to the display controller 80.

Figure 7:
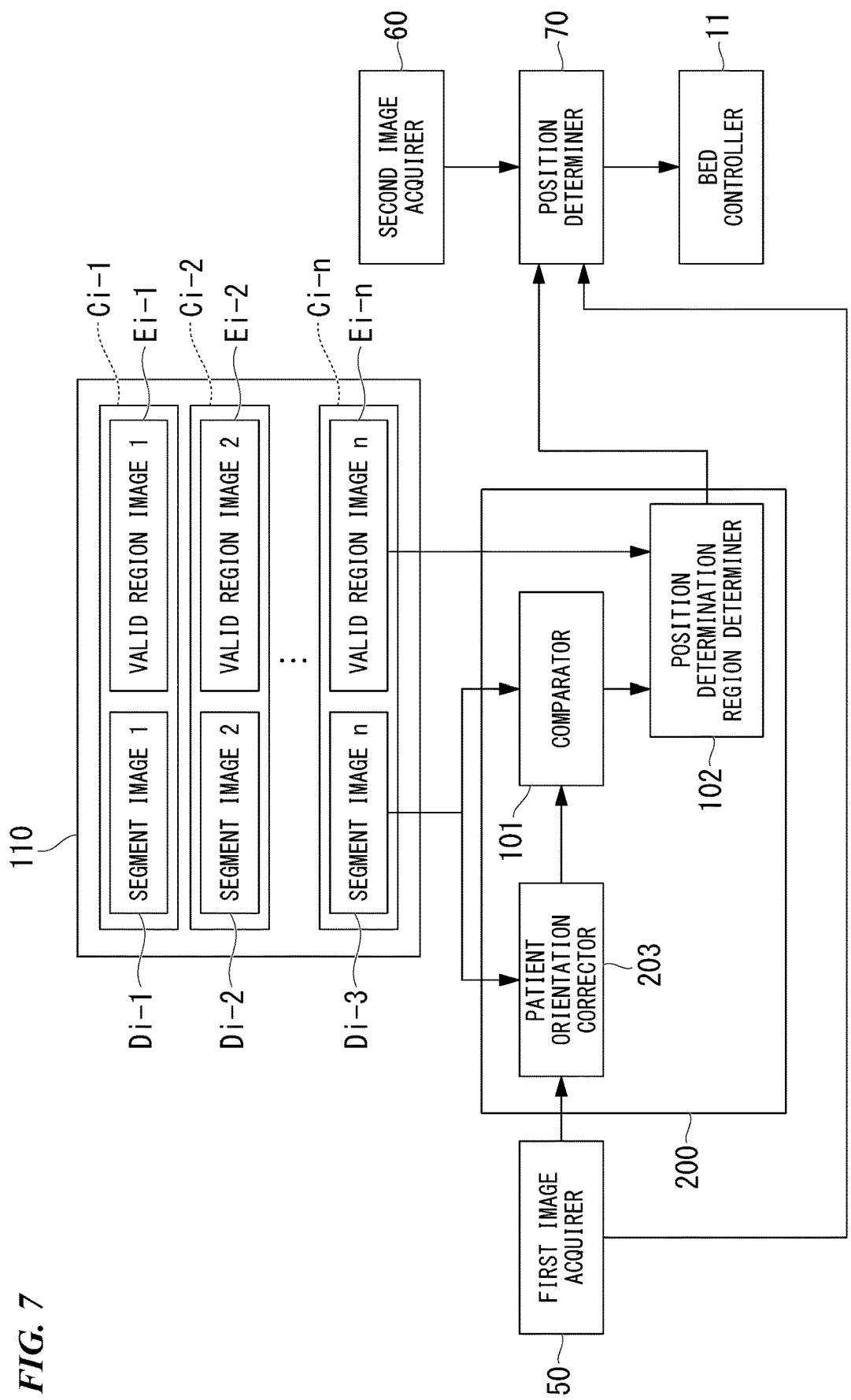
FIG. 7 is a block diagram showing a schematic configuration of a medical device and a medical image processing device of a second embodiment.

FIG. 7 is a block diagram showing a schematic configuration of the medical device and the medical image processing device 200 of the second embodiment. In FIG. 7, connection relationships between the first image acquirer 50, the second image acquirer 60, the position determiner 70, and the medical image processing device 200 constituting the medical device are shown as in the schematic configuration of the medical device and the medical image processing device 100 of the first embodiment shown in FIG. 2. Also, in FIG. 7, a connection relationship between the comparative image database 110 and the bed controller 11 related to the medical device including the medical image processing device 200 is also shown as in the schematic configuration of the medical device and the medical image processing device 100 of the first embodiment shown in FIG. 2. Also, the connection relationship between the display controller 80 constituting the medical device and other components (more specifically, the medical image processing device 200) is omitted from FIG. 7 as in the schematic configuration of the medical device and the medical image processing device 100 of the first embodiment shown in FIG. 2.

The medical image processing device 200 includes a comparator 101, a position determination region determiner 102, and a patient orientation corrector 203. The medical image processing device 200 has a configuration in which the patient orientation corrector 203 is added to the medical image processing device 100 of the first embodiment.

The comparator 101 compares a three-dimensional volume image (for example, a CT image) output by the patient orientation corrector 203 instead of a three-dimensional volume image (for example, a CT image) output by the first image acquirer 50 with each comparative image Ci (more specifically, a segment image Di) collected in the comparative image database 110. An operation and a process of the comparator 101 are similar to those of the comparator 101 provided in the medical image processing device 100 of the first embodiment, except that the CT image to be compared with the segment image Di is different. Also, the position determination region determiner 102 is similar to the position determination region determiner 102 provided in the medical image processing device 100 of the first embodiment. Accordingly, a detailed description of operations and processes of the comparator 101 and the position determination region determiner 102 will be omitted.

The patient orientation corrector 203 corrects an orientation of the three-dimensional volume image (for example, the CT image) output by the first image acquirer 50. The patient orientation corrector 203 corrects an orientation of the CT image output by the first image acquirer 50 so that an orientation of the image of the patient P shown in the CT image matches an orientation of the image of the patient P represented in the comparative image Ci collected in the comparative image database 110. For example, the patient orientation corrector 203 corrects the orientation of the CT image by performing processes such as evaluation of symmetry of the image and pattern matching of a subject image shown in the CT image. Also, the method of correcting the orientation of the CT image in the patient orientation corrector 203 is not limited to a method of evaluating the symmetry of the image or pattern matching of the subject image. The patient orientation corrector 203 outputs the CT image after the orientation correction to the comparator 101.

(Example of Method of Correcting Orientation of CT Image by Evaluating Symmetry of Image)

Here, an example of a method of correcting an orientation of a CT image by evaluating the symmetry of the image in the patient orientation corrector 203 will be described. The patient orientation corrector 203 corrects the orientation of the CT image by assuming that the human body has a shape close to left-right symmetry. In other words, the patient orientation corrector 203 corrects the orientation of the CT image in consideration of the fact that the image of the patient P shown in the CT image is more left-right symmetrical when an inclination of the patient P in the body axis direction is closer to 0 degrees. Thus, the patient orientation corrector 203 evaluates the symmetry of the image of the patient P shown in the CT image and corrects the orientation of the CT image on the basis of an evaluation result. This method can be employed when the orientation of the patient P shown in the comparative image Ci is left-right symmetrical.

Figure 8A:
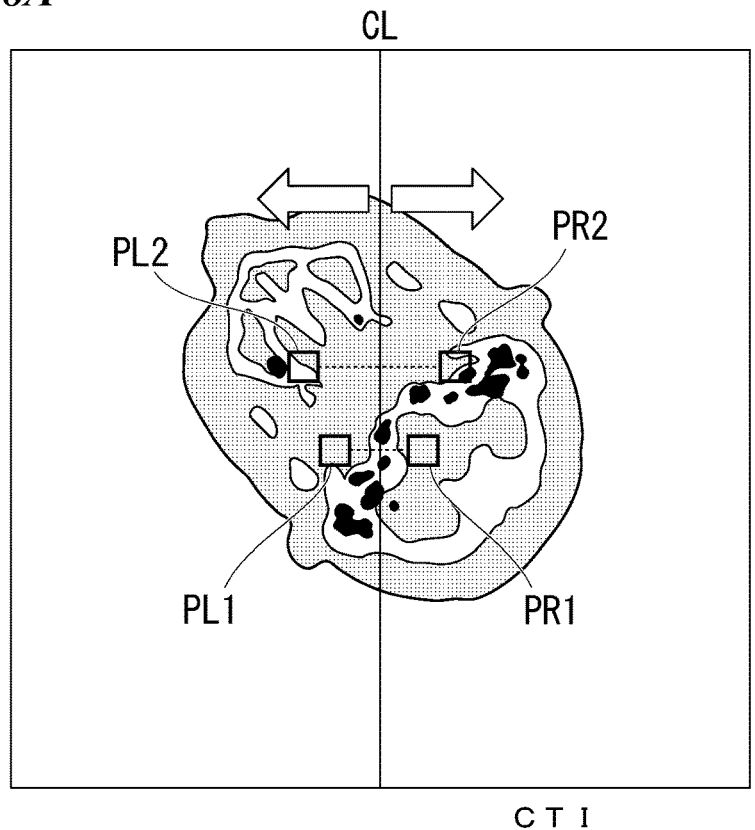
FIG. 8A is a diagram showing a concept of image orientation correction by a patient orientation corrector provided in the medical image processing device of the second embodiment.
Figure 8B:
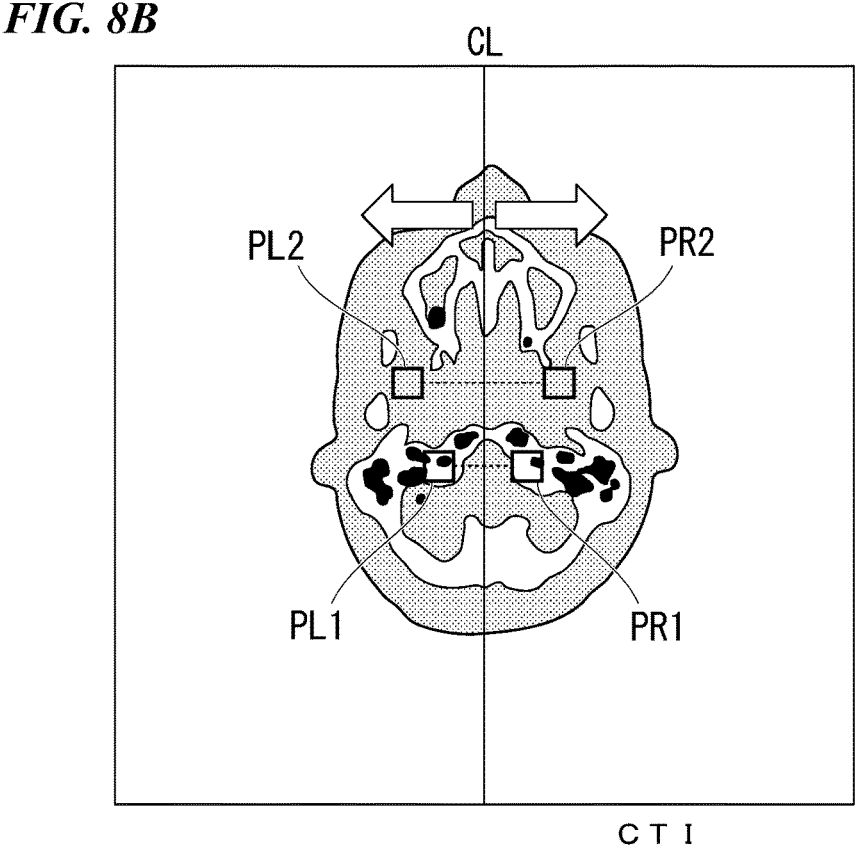
FIG. 8B is a diagram showing a concept of image orientation correction by the patient orientation corrector provided in the medical image processing device of the second embodiment.

FIGS. 8A and 8B are diagrams showing a concept of correcting the orientation of the CT image by evaluating the symmetry of the image in the patient orientation corrector 203 provided in the medical image processing device 200 of the second embodiment. In FIGS. 8A and 8B, an example of an orientation of a jaw portion of a bone (a skull) of the patient P's head shown in a CT image CTI and a degree of left-right symmetry of the CT image CTI is shown. Also, in the CT image CTI shown in FIGS. 8A and 8B, the background color is white so that the subject is more easily recognized. An example of the case where the orientation of the bone of the patient P's head is not left-right symmetrical is shown in FIG. 8A and an example of the case where the orientation of the bone of the patient P's head is symmetrical is shown in FIG. 8B. Also, in the following description, it is assumed that the upper side of an image for the image of the patient P shown in the comparative image Ci collected in the comparative image database 110 is in front of the patient P.

A degree of left-right symmetry of the CT image CTI can be obtained, for example, by evaluating (comparing) values (pixel values) of pixels spaced and located at the same distance in the left and right directions with respect to a center line CL of the patient P. This is because, if the orientation of the patient P is symmetrical, the pixel values of the pixels at positions spaced and located at the same distance in the left and right directions with respect to the center line CL will be close to each other. In other words, this is because it can be said that the image of the patient P shown in the CT image CTI is more left-right symmetrical when a difference between the pixel values of the pixels at positions spaced and located at the same distance in the left and right directions with respect to the center line CL is smaller. For example, in the CT image CTI of FIG. 8A, because the orientation of the bone of the patient P's head that is shown is not left-right symmetrical, a difference between a pixel value of a pixel PL1 located on the left side of the center line CL and a pixel value of a pixel PR1 located on the right side of the center line CL is large. Likewise, in the CT image CTI of FIG. 8A, the difference between the pixel value of a pixel PL2 located on the left side of the center line CL and the pixel value of a pixel PR2 located on the right side of the center line CL is also large.

Thus, the patient orientation corrector 203 corrects the orientation of the CT image CTI by rotating the entire CT image CTI so that the difference between the pixel values of the pixels at positions spaced and located at the same distance in the left and right directions with respect to the center line CL is set to a small value less than or equal to a prescribed value. Thereby, for example, as shown in the CT image CTI in FIG. 8B, the orientation of the bone of the patient P's head that is shown becomes left-right symmetrical. In the CT image CTI of FIG. 8B, because the orientation of the bone of the patient P's head that is shown is left-right symmetrical, the difference between the pixel value of the pixel PL1 located on the left side of the center line CL and the pixel value of the pixel PR1 located on the right side of the center line CL is small. Also, likewise, in the CT image CTI of FIG. 8B, a difference between a pixel value of the pixel PL2 located on the left side of the center line CL and a pixel value of the pixel PR2 located on the right side of the center line CL is also small.

In this way, the patient orientation corrector 203 corrects the orientation of the CT image CTI by comparing the pixel values of the pixels at positions spaced and located at the same distance in the left and right directions with respect to the center line CL in the image of the patient P shown in the CT image CTI. An example of the process of the patient orientation corrector 203 in this case will be described below. FIGS. 9A, 9B, 9C, and 9D are diagrams schematically showing an example of the orientation correction process on the CT image CTI in the patient orientation corrector 203 provided in the medical image processing device 200 of the second embodiment. FIGS. 9A, 9B, 9C, and 9D sequentially show a flow of a processing procedure for correcting the orientation of the CT image CTI in the patient orientation corrector 203. In each of the images shown in FIGS. 9A, 9B, 9C, and 9D, the background color is white so that the subject is more easily recognized.

(Procedure P-1): The patient orientation corrector 203 acquires a CT image CTI output by the first image acquirer 50. In procedure P-1 of FIG. 9A, a state in which the patient orientation corrector 203 has acquired a CT image CTI-B (a three-dimensional volume image) before correction in which the orientation of the jaw portion of the bone (the skull) of the patient P's head is not left-right symmetrical is shown.

Figure 9A:
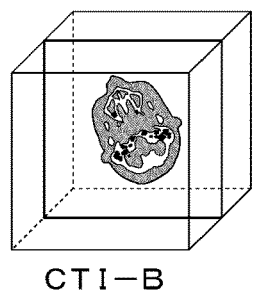
FIG. 9A is a diagram schematically showing an example of an image orientation correction process of the patient orientation corrector provided in the medical image processing device of the second embodiment.
Figure 9B:
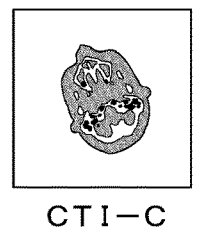
FIG. 9B is a diagram schematically showing an example of an image orientation correction process of the patient orientation corrector provided in the medical image processing device of the second embodiment.

(Procedure P-2): The patient orientation corrector 203 extracts one image for evaluating the symmetry (a degree of left-right symmetry) of the image of the patient P shown in the CT image CTI-B from the acquired CT image CTI-B. One image for evaluating this symmetry can be extracted, for example, by cutting out the center position of the CT image CTI-B. Hereinafter, the one image extracted by the patient orientation corrector 203 by cutting out the center position of the CT image CTI-B is referred to as a "cut-out image CTI-C." Procedure P-2 of FIG. 9B shows an example of the cut-out image CTI-C extracted by the patient orientation corrector 203.

Figure 9C:
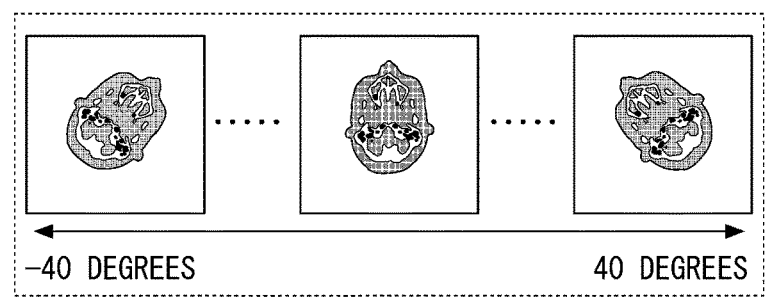
FIG. 9C is a diagram schematically showing an example of an image orientation correction process of the patient orientation corrector provided in the medical image processing device of the second embodiment.
Figure 9D:
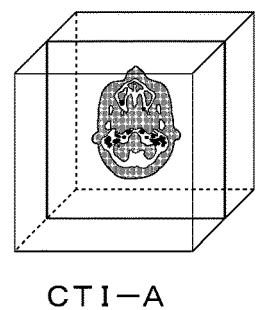
FIG. 9D is a diagram schematically showing an example of an image orientation correction process of the patient orientation corrector provided in the medical image processing device of the second embodiment.

(Procedure P-3): The patient orientation corrector 203 performs an evaluation process of evaluating symmetry while rotating the cut-out image CTI-C within a range of a prescribed angle. Procedure P-3 of FIG. 9C shows a state in which the evaluation process is performed while the cut-out image CTI-C rotates within an angle range of −40 degrees to 40 degrees. The patient orientation corrector 203 determines an angle at which it is considered that left-right symmetry is largest (a degree of left-right symmetry is high) in the evaluation process in procedure P-3. In other words, the angle for correcting the orientation of the CT image CTI-B is determined.

(Procedure P-4): The patient orientation corrector 203 corrects the orientation of the CT image CTI-B by rotating the entire CT image CTI-B at the angle determined in the evaluation process in procedure P-3. In procedure P-4 of FIG. 9D, an example of the CT image CTI-A after correction in which the entire CT image CTI-B (three-dimensional volume image) acquired in procedure P-1 is rotated at the angle determined in procedure P-3 is shown.

In the flow of such procedures, the patient orientation corrector 203 corrects the orientation of the CT image CTI-B (before correction) output by the first image acquirer 50 and outputs the corrected CT image CTI-A (after correction) to the comparator 101. Thereby, in the medical image processing device 200, the comparator 101 compares the CT image CTI-A whose orientation has been corrected by the patient orientation corrector 203 with the segment image Di and the position determination region determiner 102 determines a position determination region with respect to the CT image CTI-A whose orientation has been corrected by the patient orientation corrector 203.

In the flow of the procedures for the orientation correction process on the CT image CTI in the patient orientation corrector 203 shown in FIGS. 9A, 9B, 9C, and 9D, the case where one cut-out image CTI-C is cut out from the CT image CTI-B and the angle for correcting the orientation of the CT image CTI is determined has been described. However, the number of cut-out images CTI-C cut out from the CT image CTI-B to determine the angle for correcting the orientation of the CT image CTI is not limited to one. A plurality of cut-out images CTI-C may be cut out from the CT image CTI-B and the angle for correcting the orientation of the CT image CTI may be determined. In this case, the orientation of the CT image CTI can be corrected with higher accuracy by integrating the angles determined in the evaluation process with respect to the cut-out images CTI-C.

Here, an evaluation process (a method of evaluating the degree of left-right symmetry) in procedure P-3 shown in FIG. 9C will be described. As shown in FIGS. 8A and 8B, it is necessary to determine the center line CL as a reference when the degree of left-right symmetry of the CT image CTI is evaluated by comparing pixel values of pixels spaced and located at the same distance in the left and right directions with respect to the center line CL of the image of the patient P shown in the CT image CTI. However, the patient P shown in the CT image CTI at the planning stage of radiation treatment is not always shown at the center position of the CT image CTI. Thus, it is necessary to determine the center position of the patient P by estimating the center position of the patient P or using an evaluation value having position invariance before the evaluation process is performed.

As a method of estimating the center position of the patient P, for example, there is a method using a classifier in which an image pattern near the center of the patient P is machine-learned in advance. In the case of this method, an image pattern cut out from the position of each pixel constituting the CT image before correction is input to the classifier and the position where an output of the classifier is maximized can be estimated as the center position of the patient P. Thereby, the patient orientation corrector 203 can compare the pixel values of the pixels with respect to the center line CL determined on the basis of the estimated center position and evaluate the symmetry of the image of the patient P shown in the CT image (the degree of left-right symmetry).

As a method using an evaluation value having position invariance, for example, there is a method of performing a Fourier transform on a CT image and using an amplitude value in a frequency domain. In the case of this method, as a method using an evaluation value having position invariance, for example, there is a method of performing a Fourier transform on a CT image and using a result thereof. In the case of this method, the center position of the patient P can be determined using the amplitude value of the frequency domain obtained in the Fourier transform as an evaluation value having position invariance. For example, assuming that the Fourier transform of the image I(x, y) is F(u, v), the Fourier transform F(u, v) is also axisymmetric at the center when the image I (x, y) is axisymmetric at the center of the image. From this, the amplitude value is expressed by the following Eq. (1).

[Math. 1]

$$\left|\mathcal{F}\left(\frac{N}{2} - du, v\right)\right| = \left|\mathcal{F}\left(\frac{N}{2} + du, v\right)\right| \quad (1)$$

Even if the image is translationally moved, the amplitude value expressed by the above Eq. (1) is always valid because an amplitude does not change with only a shift of a phase in the frequency domain. From this, the patient orientation corrector 203 can evaluate the symmetry (the degree of left-right symmetry) of the image of the patient P shown in the CT image regardless of a position where the patient P within the CT image is shown by evaluating the symmetry of the amplitude value in the frequency domain.

(Example of Method of Correcting Orientation of CT Image Using Pattern Matching of Subject Image)

Next, an example of a method of correcting an orientation of a CT image using pattern matching of a subject image in the patient orientation corrector 203 will be described. When the orientation of the CT image is corrected using the pattern matching of the subject image, a plurality of images in which the orientations of the patients are aligned in advance are provided. Here, the images to be provided may be images of a plurality of unspecified patients. Also, a classifier that has learned the image pattern using each image provided in advance as a learning image is prepared. The classifier prepared here is allowed to learn two classes of a correct image pattern and a non-correct image pattern. At this time, for example, the learning image is randomly moved or rotated to generate any image pattern. The classifier is allowed to learn an image pattern with a small amount of deviation from an initial value as a correct image pattern. On the other hand, the classifier is allowed to learn an image pattern with a large amount of deviation from the initial value as a non-correct image pattern.

When the orientation of the patient P is estimated, the patient orientation corrector 203 cuts out an image pattern while changing the position and orientation of the CT image output by the first image acquirer 50, inputs the image pattern to the classifier, and estimates the orientation of the patient P shown in the CT image on the basis of a determination result of the classifier. When the determination result of the classifier is the correct image pattern, the patient orientation corrector 203 corrects the orientation of the CT image to a position or an orientation obtained by cutting out the image pattern from the CT image.

In this way, the patient orientation corrector 203 corrects the orientation of the CT image by performing pattern matching using the classifier that has learned the image pattern in advance.

Figure 10:
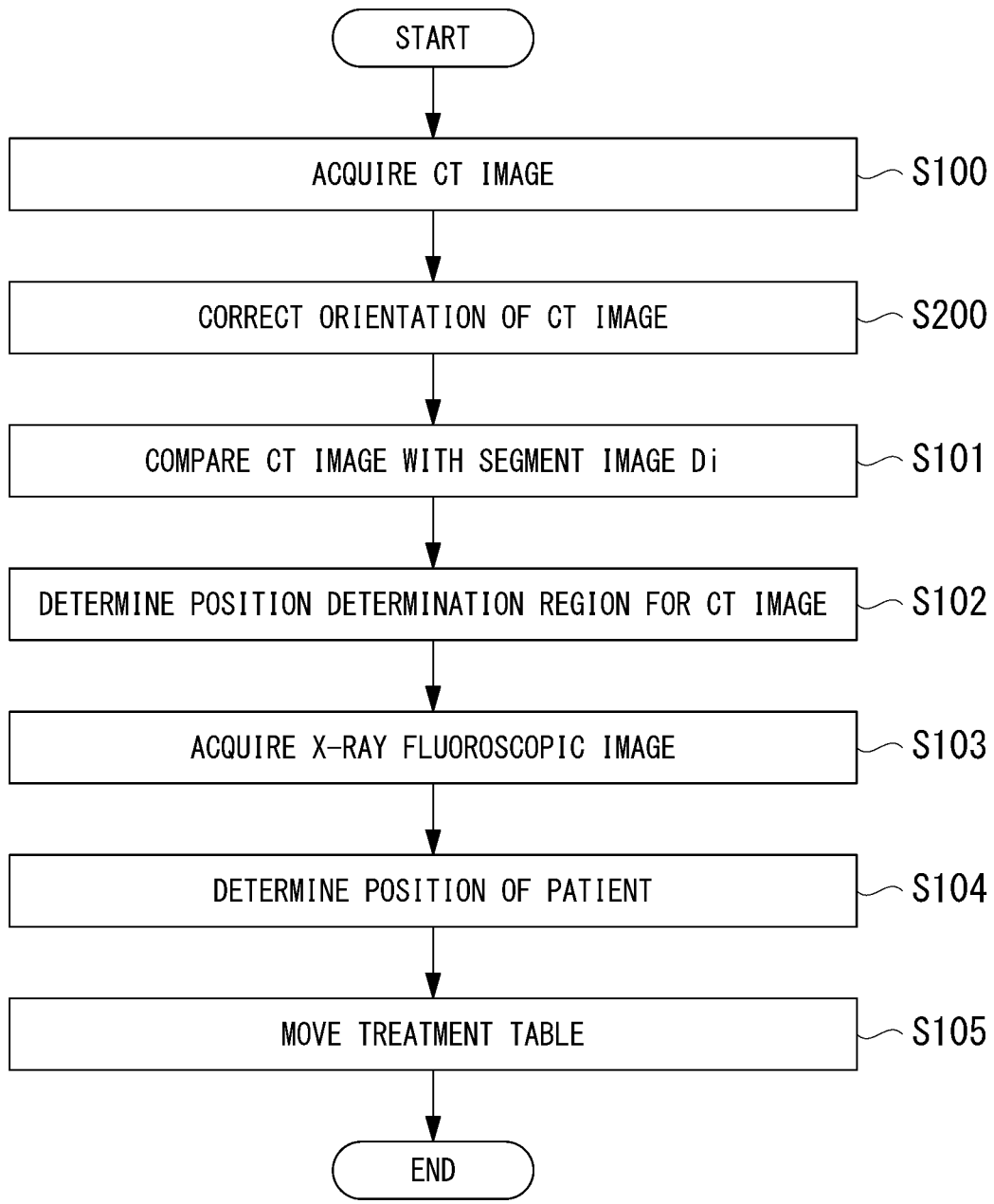
FIG. 10 is a flowchart showing the flow of an operation in a treatment system of the second embodiment.

Next, the operation of the treatment system 2 will be schematically described. FIG. 10 is a flowchart showing a flow of the operation in the treatment system 2 of the second embodiment. In the flowchart of the treatment system 2 shown in FIG. 10, step S200 is inserted between steps S101 and S102 in the flowchart of the treatment system 1 of the first embodiment shown in FIG. 5. In other words, in the treatment system 2, a process other than step S200 is similar to the process of the treatment system 1 of the first embodiment.

When the treatment system 2 starts an operation, the first image acquirer 50 acquires a CT image (step S100). The first image acquirer 50 outputs the acquired CT image to the position determiner 70 and the patient orientation corrector 203 provided in the medical image processing device 200.

Subsequently, the patient orientation corrector 203 corrects an orientation of the CT image output by the first image acquirer 50 (step S200). The patient orientation corrector 203 outputs a corrected CT image to the comparator 101.

Hereinafter, as in the flowchart of the treatment system 1 of the first embodiment shown in FIG. 5, the comparator 101 compares the corrected CT image output by the patient orientation corrector 203 with a segment image Di (step S101) and the position determination region determiner 102 determines a position determination region for the corrected CT image (step S102). As in the flowchart of the treatment system 1 of the first embodiment shown in FIG. 5, the second image acquirer 60 acquires an X-ray fluoroscopic image PI (step S103), the position determiner 70 obtains an amount of movement of the treatment table 10 by determining the position of the patient P (step S104), and the bed controller 11 causes the treatment table 10 to be moved on the basis of information of the amount of movement output by the position determiner 70 (step S105). Thereby, the current position of the patient P fixed on the treatment table 10 is moved to a position suitable for performing radiation treatment.

As described above, in the medical image processing device 200, after the orientation of the CT image is corrected by the patient orientation corrector 203, the corrected CT image and the segment image Di are compared by the comparator 101, and the position determination region determiner 102 determines the position determination region within the CT image. Thereby, also in the medical image processing device 200, as in the medical image processing device 100 of the first embodiment, for example, it is possible to automatically set a position determination region similar to a region of interest used in position alignment of patients subjected to the treatment of the same treatment portion in the previous radiation treatment without designating a region of interest when the radiation treatment practitioner (the doctor or the like) operates a user interface such as the operator (not shown) to align the position of the patient P. Moreover, in the medical image processing device 200, because the patient orientation corrector 203 performs correction so that the orientation of the image of the patient P shown in the three-dimensional volume image (for example, the CT image) is aligned with the orientation of the image of the patient P represented in the segment image Di, it is possible to set the position determination region with higher accuracy than in the medical image processing device 100 of the first embodiment. Thereby, in the medical device including the medical image processing device 200, the direction of the patient P to be treated in the radiation treatment can be directed to the position determined by the position determiner 70, i.e., the patient P can be directed in a direction suitable for radiating the treatment beam B. In this way, in the treatment system 2 provided with the medical device including the medical image processing device 200, the position determination for the patient P in the radiation treatment can be performed with high accuracy.

Also, in the above description, the case where the patient orientation corrector 203 corrects the orientation of the CT image by rotating the entire CT image has been described. However, the correction of the CT image by the patient orientation corrector 203 is not limited to the entire CT image. For example, the patient orientation corrector 203 may correct the orientation of only the subject image shown in the CT image, i.e., the orientation of only the patient P.

As described above, the medical image processing device 200 may further include the patient orientation corrector 203 configured to correct an orientation of the first image (a three-dimensional volume image (for example, a CT image)) so that an orientation of the patient P shown in the first image is aligned with an orientation of a patient P shown in the comparative image Ci, wherein the comparator 101 may compare the first image in which the orientation is corrected by the patient orientation corrector 203 with the comparative image Ci.

Third Embodiment

Hereinafter, a third embodiment will be described. Also, a configuration of a treatment system provided with a medical device including a medical image processing device of the third embodiment is a configuration obtained by replacing the medical image processing device 100 with the medical image processing device of the third embodiment (hereinafter, referred to as a "medical image processing device 300") in the configuration of the treatment system 1 provided with the medical device including the medical image processing device 100 of the first embodiment shown in FIG. 1. In the following description, a treatment system provided with a medical device including the medical image processing device 300 is referred to as a "treatment system 3."

Also, in the following description, components similar to those of the treatment system 1 provided with the medical device including the medical image processing device 100 of the first embodiment among components of the treatment system 3 provided with the medical device including the medical image processing device 300 are denoted by the same reference signs and a detailed description of the similar components will be omitted. In the following description, only a configuration, an operation, and a process of the medical image processing device 300, which is a component different from the medical image processing device 100 of the first embodiment, will be described.

In the treatment system 3, a combination of the first image acquirer 50, the second image acquirer 60, the position determiner 70, the display controller 80, and the medical image processing device 300 is an example of a "medical device" in the claims. Also, for example, a hardware processor such as a CPU and a storage device (a storage device including a non-transitory storage medium) storing a program (software) are provided for some or all of the functions of the components provided in the medical device and the functions of the components may be implemented by the processor executing the program. Also, some or all of the functions of the components provided in the medical device may be implemented by hardware (including a circuit unit; circuitry) such as an LSI circuit, an ASIC, an FPGA, or a GPU or the functions of the components may be implemented by software and hardware in cooperation. Also, some or all of the functions of the components provided in the medical device may be implemented by a dedicated LSI circuit. Here, the program (software) may be pre-stored in a storage device (a storage device including a non-transitory storage medium) provided in the treatment system 3 such as a ROM, a RAM, an HDD, or a flash memory or may be stored in a removable storage medium (a non-transitory storage medium) such as a DVD or a CD-ROM and installed in the storage device provided in the treatment system 3 when the storage medium is mounted in a drive device provided in the treatment system 3. Also, the program (software) may be downloaded in advance from another computer device via the network and installed in the storage device provided in the treatment system 3.

Like the medical image processing device 100 of the first embodiment, the medical image processing device 300 determines a position determination region for use in position alignment of a patient P with respect to a CT image output by the first image acquirer 50 with reference to a comparative image collected in a comparative image database 110. At this time, the medical image processing device 300 determines the position determination region for use in the position alignment of the patient P in consideration of a beam range of the treatment beam B to be radiated in the radiation treatment. Like the medical image processing device 100 of the first embodiment, the medical image processing device 300 outputs information of the determined position determination region to the position determiner 70. Also, the medical image processing device 300 generates an image for confirming the region of interest for use in position alignment of the patient P preferentially when the beam range of the treatment beam B is taken into consideration and outputs the image to the display controller 80.

Figure 11:
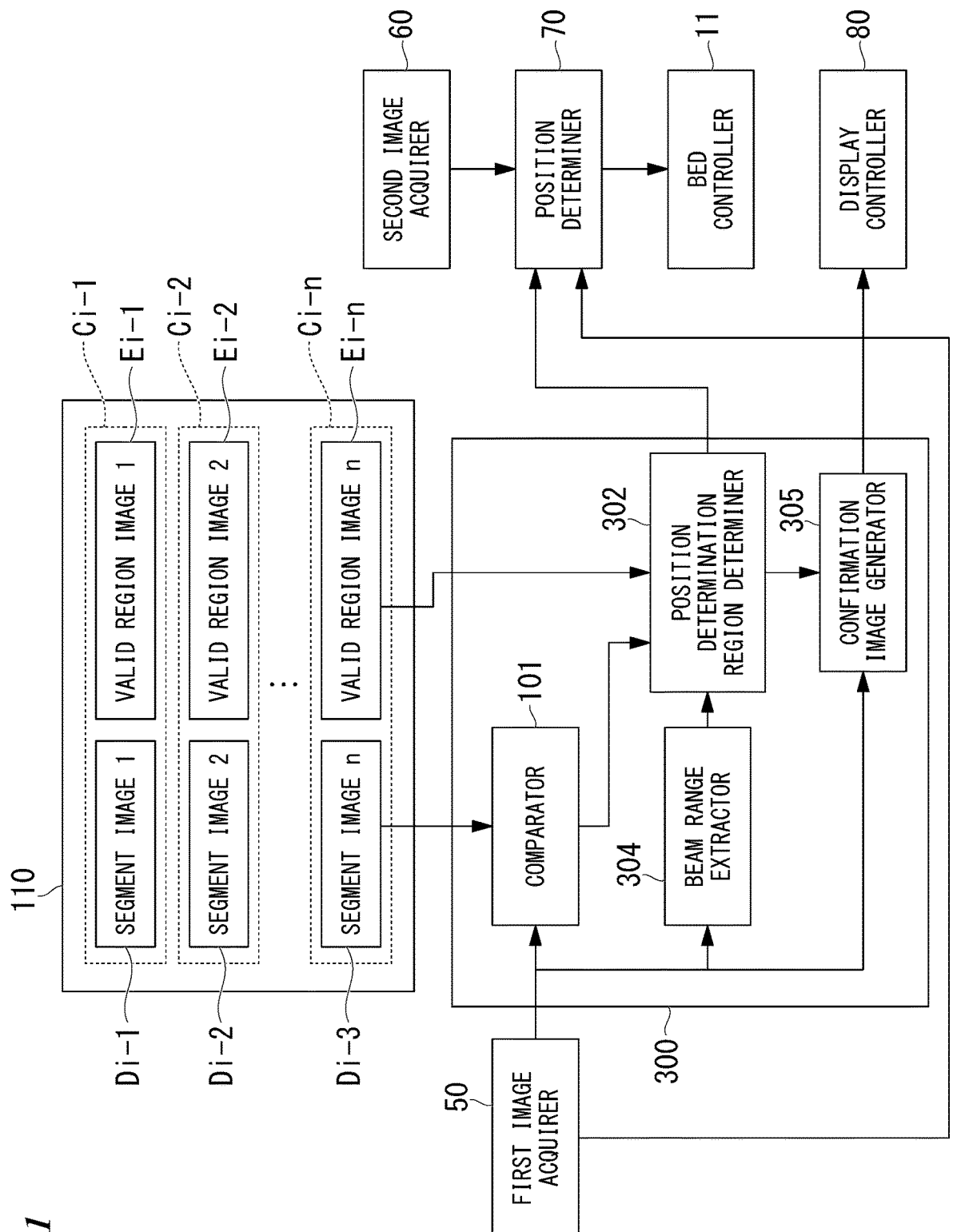
FIG. 11 is a block diagram showing a schematic configuration of a medical device and a medical image processing device of a third embodiment.

FIG. 11 is a block diagram showing a schematic configuration of the medical device and the medical image processing device 300 of the third embodiment. In FIG. 11, connection relationships between the first image acquirer 50, the second image acquirer 60, the position determiner 70, the display controller 80, and the medical image processing device 300 constituting the medical device are shown. Also, the connection relationship between the comparative image database 110 and the bed controller 11 related to the medical device including the medical image processing device 300 is also shown in FIG. 11 as in the schematic configuration of the medical device and the medical image processing device 100 of the first embodiment shown in FIG. 2. Also, the connection relationship between the second image acquirer 60 constituting the medical device and another component (more specifically, the radiation detector 30) and a connection relationship between the display controller 80 and another component (more specifically, the display device 81) are omitted from FIG. 11.

The medical image processing device 300 includes a comparator 101, a position determination region determiner 302, a beam range extractor 304, and a confirmation image generator 305. The medical image processing device 300 has a configuration in which the position determination region determiner 102 provided in the medical image processing device 100 of the first embodiment is replaced with the position determination region determiner 302 and the beam range extractor 304 and the confirmation image generator 305 are added.

The beam range extractor 304 acquires a three-dimensional volume image (for example, a CT image) output by the first image acquirer 50 and information of a beam range which is an arrival distance of the treatment beam B from treatment plan information (information predetermined at a treatment planning stage) and extracts a prescribed range to be preferentially used when the beam range is considered in the position alignment of the patient P. For example, the beam range extractor 304 acquires information of the beam range of the treatment beam B on the basis of information such as a position of a treatment portion, an irradiation direction of the treatment beam B, and an irradiation intensity determined in advance with respect to the CT image. The beam range extractor 304 extracts a range of a prescribed distance around the treatment beam B to the beam range of the treatment beam B on the basis of the acquired information of the beam range of the treatment beam B. In the following description, the range of the beam extracted by the beam range extractor 304 is referred to as a "beam range." For example, assuming that the beam range of the treatment beam B is one path, the beam range extractor 304 extracts a range of a cylinder having a length to the beam range centered on the treatment beam B as the beam range. The beam range extractor 304 outputs information of the extracted beam range to the position determination region determiner 302.

Like the position determination region determiner 102 provided in the medical image processing device 100 of the first embodiment, the position determination region determiner 302 determines a range of the valid region included within the CT image as the position determination region on the basis of information of the comparison result output by the comparator 101. Further, the position determination region determiner 302 determines the range of a valid region to be preferentially used in the position alignment of the patient P within the determined range of the position determination region as a preferential position determination region on the basis of information of the beam range output by the beam range extractor 304. In other words, the position determination region determiner 302 determines the range of the valid region in the position alignment of the patient P present on the path to the beam range of the treatment beam B among valid regions determined on the basis of the information of the comparison result output by the comparator 101 as the preferential position determination region. At this time, the position determination region determiner 302 selects a valid region within the beam range from the valid region determined on the basis of information of the comparison result output by the comparator 101 and determines a range of the selected valid region as the preferential position determination region. The preferential position determination region determined here becomes a range of a valid region from the treatment portion to the side of the treatment beam irradiation gate 40, i.e., the front side of the position determination region. In other words, because the preferential position determination region is located behind the beam range of the treatment beam B, i.e., at a position where the treatment beam B does not reach, the preferential position determination region has a range obtained by excluding a valid region that does not necessarily need to be aligned in the position alignment of the patient P.

Also, the method of determining the preferential position determination region in the position determination region determiner 302 is not limited to a method of selecting a range of a valid region included within the beam range after determining the position determination region and determining the selected range of the valid region as the preferential position determination region as described above. For example, the position determination region determiner 302 may determine the range of the valid region included within the beam range output by the beam range extractor 304 as the preferential position determination region on the basis of the information of the comparison result output by the comparator 101 in a concept similar to that of a method when the range of the valid region is determined to be the position determination region. Alternatively, the information of the comparison result of the comparator 101 may be calculated in a narrowing-down process within the beam range. Thereby, it is possible to expect the effect of shortening the calculation time period in the comparator 101.

The position determination region determiner 302 outputs information indicating the range of the position determination region within the determined CT image and information indicating the range of the determined preferential position determination region to the position determiner 70.

Thereby, the position determiner 70 can determine a position of the patient P more suitable for performing radiation treatment with higher accuracy on the basis of the information indicating the range of the preferential position determination region output by the position determination region determiner 302. For example, in the X-ray fluoroscopic image PI, the bones on the front side and the back side of the treatment portion are similarly photographed. That is, in the X-ray fluoroscopic image PI, photography is performed in a state in which it is not easy to classify the position of the bone in a depth direction. Even in the X-ray fluoroscopic image PI in such a state, the position determiner 70 can determine the position of the patient P by excluding a valid region of the bone behind the beam range of the treatment beam B in the X-ray fluoroscopic image PI from the valid region for use in the position alignment of the patient P on the basis of the information indicating the range of the preferential position determination region.

Also, the position determination region determiner 302 may output only information indicating the range of the preferential position determination region within the determined CT image to the position determiner 70. In this case, the position determiner 70 can determine the position of the patient P more suitable for performing radiation treatment using information indicating the range of the preferential position determination region output by the position determination region determiner 302 as information indicating a range of the position determination region output by the position determination region determiner 102 provided in the medical image processing device 100 of the first embodiment. Further, in this case, because it is only necessary for the position determination region determiner 302 to determine only the preferential position determination region, it is possible to speed up the process of determining the position determination region and reduce the processing load.

Also, the position determination region determiner 302 outputs the preferential position determination region within the determined CT image to the confirmation image generator 305.

The confirmation image generator 305 generates a confirmation image obtained by highlighting and superimposing the preferential position determination region output by the position determination region determiner 302 within the three-dimensional volume image (for example, the CT image) output by the first image acquirer 50. The confirmation image generator 305 outputs the generated confirmation image to the display controller 80. Thereby, the display controller 80 causes the display device 81 to display the confirmation image output by the confirmation image generator 305.

Also, like the position determination region determiner 102 provided in the medical image processing device 100 of the first embodiment, the position determination region determiner 302 in the medical image processing device 300 may output the CT image output by the first image acquirer 50 and information of the position determination region and information of the preferential position determination region within the determined CT image to the display controller 80. In this case, the display controller 80 can also be configured to generate a confirmation image and cause the display device 81 to display the confirmation image. In the case of this configuration, the medical image processing device 300 may be configured not to include the confirmation image generator 305.

(Example of Confirmation Image)

Figure 12:
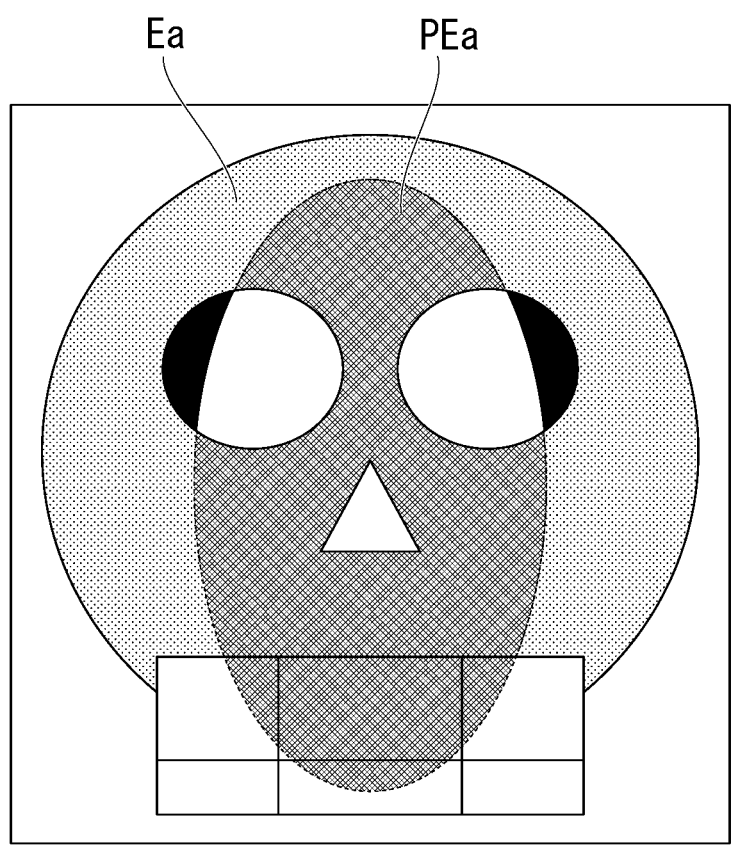
FIG. 12 is a diagram showing an example of a confirmation image generated by a confirmation image generator provided in the medical image processing device of the third embodiment.

Here, an example of a confirmation image generated by the confirmation image generator 305 will be described. FIG. 12 is a diagram showing an example of the confirmation image generated by the confirmation image generator 305 provided in the medical image processing device 300 of the third embodiment. In FIG. 12, an example of an image (a confirmation image) showing the range of the preferential position determination region determined by the position determination region determiner 302 within the range of the bone (the skull) of the patient P's head shown in the CT image is shown. Also, in the confirmation image VRI (the CT image) shown in FIG. 12, the background color is white so that the subject is more easily recognized.

For example, the confirmation image generator 305 generates a confirmation image in which a region of interest to be used preferentially can be visually confirmed when a radiation treatment practitioner (a doctor or the like) considers the beam range in the position alignment of the patient P by highlighting the region of the preferential position determination region within the CT image (making the region of the preferential position determination region within the CT image conspicuous). For example, the confirmation image generator 305 generates a confirmation image in which a portion highlighted by making the color of the region of the preferential position determination region different from those of other position determination regions is made conspicuous.

In FIG. 12, an example of a confirmation image VRI (a CT image) in which a preferential position determination region PEa for use in position alignment is highlighted (made conspicuous) when the treatment beam B is radiated from the front of the patient P's face in a prescribed range (i.e., scanning irradiation) in the case where the valid region Ea is allocated to the entire skull of the patient P shown within the CT image CTI (see, for example, FIG. 6D) is shown. In an example of the confirmation image VRI (the CT image) shown in FIG. 12, the color of the preferential position determination region PEa from the treatment portion to the side (front side) of the treatment beam irradiation gate 40 is made different from the color of the valid region Ea behind the treatment portion (for example, the valid region Ea is blue, the preferential position determination region PEa is red, or the like) and therefore is highlighted (made conspicuous). The confirmation image generator 305 generates such a confirmation image and outputs the confirmation image to the display controller 80, so that the display controller 80 causes the display device 81 to display the confirmation image. Thereby, for example, the radiation treatment practitioner (the doctor or the like) can more clearly and visually confirm the preferential position determination region PEa within the valid region Ea.

Also, the confirmation image showing the valid region Ea or the preferential position determination region PEa in the CT image can be rotated by, for example, the radiation treatment practitioner (the doctor or the like) operating the user interface such as the operator (not shown). Thereby, for example, the radiation treatment practitioner (the doctor or the like) can rotate the confirmation image to confirm the valid region Ea and the preferential position determination region PEa from various angles.

(Another Example of Confirmation Image)

Figure 13:
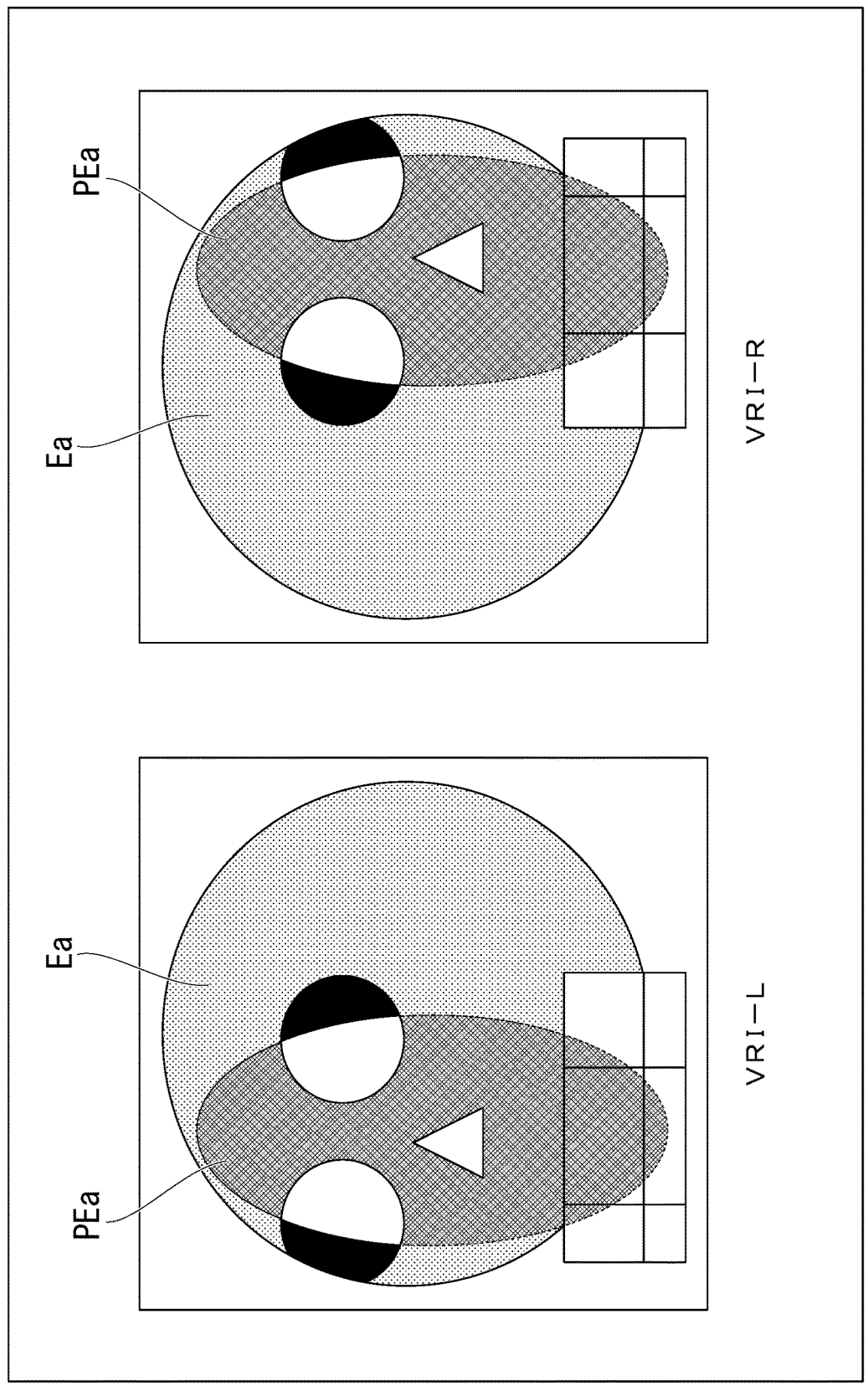
FIG. 13 is a diagram showing another example of a confirmation image generated by the confirmation image generator provided in the medical image processing device of the third embodiment.

FIG. 13 is a diagram showing another example of the confirmation image generated by the confirmation image generator 305 provided in the medical image processing device 300 of the third embodiment. In FIG. 13, an example of an image (a confirmation image) indicating the range of the preferential position determination region PEa determined by the position determination region determiner 302 within the range of the bone (the skull) of the patient P's head shown in each DRR image reconstructed from the CT image is shown. Also, in the confirmation image VRI (the DRR image) shown in FIG. 13, the background color is white so that the subject is more easily recognized.

For example, a case where the image confirmed by the radiation treatment practitioner (the doctor or the like) in the position alignment of the patient P is an X-ray fluoroscopic image PI of the inside of the body of the patient P currently fixed on the treatment table 10 output by each of the two radiation detectors 30 is also conceivable. In this case, the confirmation image generator 305 generates, for example, a DRR image reconstructed in correspondence with each of the two radiation sources 20 and generates a confirmation image showing the preferential position determination region PEa on each generated DRR image. Also, in this case, for example, the confirmation image generator 305 generates a confirmation image in which a portion highlighted in each DRR image is made conspicuous, for example, by making the color of the preferential position determination region PEa within each DRR image different from the color of the valid region Ea.

In FIG. 13, an example of a confirmation image VRI (a DRR image) in which the preferential position determination region PEa for use in position alignment when the treatment beam B is radiated from the front of the patient P's face in a prescribed range according to scanning irradiation is highlighted (made conspicuous) in each DRR image reconstructed when the valid region Ea is allocated to the entire skull of the patient P shown within the CT image is shown. The DRR image on the left side of FIG. 13 is, for example, an example of a confirmation image VRI-L (a DRR image) corresponding to an X-ray fluoroscopic image PI captured by a photography device including a set of a radiation source 20-1 and a radiation detector 30-1 in the treatment system 1. Also, the DRR image on the right side of FIG. 13 is, for example, an example of a confirmation image VRI-R (a DRR image) corresponding to an X-ray fluoroscopic image PI captured by a photography device including a set of a radiation source 20-2 and a radiation detector 30-2 in the treatment system 1. In an example of each confirmation image VRI (the DRR image) shown in FIG. 13, the color of the preferential position determination region PEa from the treatment portion to the side (front side) of the treatment beam irradiation gate 40 is made different from the color of the valid region Ea behind the treatment portion (for example, the valid region Ea is blue, the preferential position determination region PEa is red, or the like) and therefore is highlighted (made conspicuous). The confirmation image generator 305 generates each confirmation image as described above and outputs the confirmation image to the display controller 80, so that the display controller 80 causes the display device 81 to display the confirmation image. Thereby, for example, the radiation treatment practitioner (the doctor or the like) can compare the X-ray fluoroscopic image PI of the inside of the body of the patient P currently fixed on the treatment table 10 with each corresponding confirmation image (DRR image) and more clearly and visually confirm the preferential position determination region PEa within the valid region Ea shown in the confirmation image (the DRR image). Also, the confirmation image (the DRR image) may be created on the basis of only the preferential position determination region PEa within the CT image. Thereby, it is possible to compare monochrome images of the X-ray fluoroscopic image PT and the DRR image as in the conventional radiation treatment while clarifying the preferential position determination region PEa.

Figure 14:
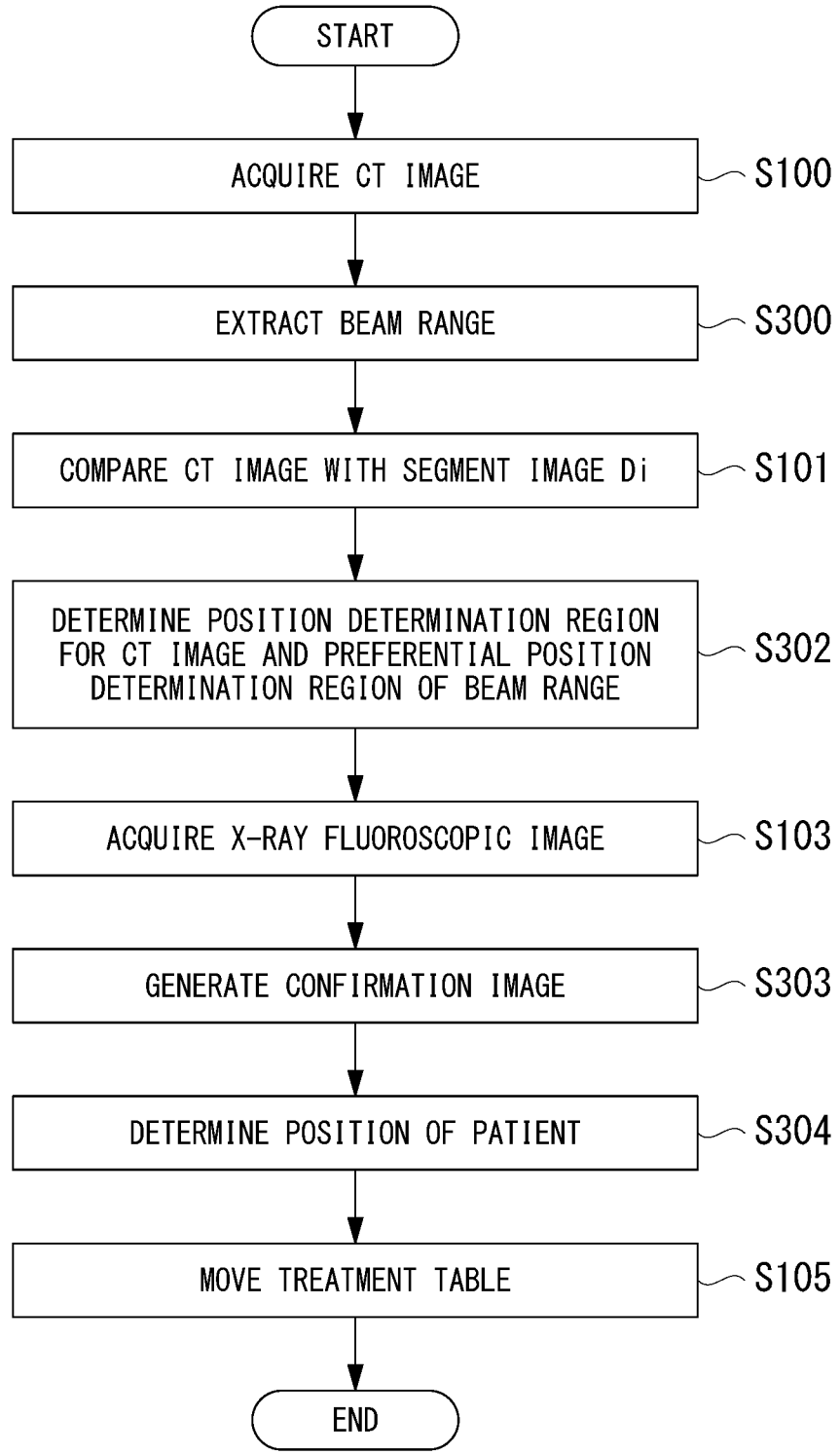
FIG. 14 is a flowchart showing a flow of an operation in a treatment system of the third embodiment.

Next, an operation of the treatment system 3 will be schematically described. FIG. 14 is a flowchart showing a flow of an operation in the treatment system of the third embodiment. The flowchart of the treatment system 3 shown in FIG. 14 may include a process similar to the process in the flowchart of the treatment system 1 of the first embodiment shown in FIG. 5. Accordingly, in the following description, in the operation of the treatment system 3, a detailed description of a process similar to the process in the treatment system 1 of the first embodiment will be omitted.

When the treatment system 3 starts an operation, the first image acquirer 50 acquires a CT image (step S100). The first image acquirer 50 outputs the acquired CT image to the position determiner 70 and the comparator 101, the beam range extractor 304, and the confirmation image generator 305 included in the medical image processing device 300.

Subsequently, the beam range extractor 304 acquires information of a beam range of the treatment beam B from the CT image output by the first image acquirer 50 and extracts the beam range (step S300). The beam range extractor 304 outputs information of the extracted beam range to the position determination region determiner 302.

Subsequently, the comparator 101 compares the CT image output by the first image acquirer 50 with a segment image Di of each treatment portion collected in the comparative image database 110 (step S101). The comparator 101 outputs information of a comparison result to the position determination region determiner 102. Also, the processing of step S101 in the comparator 101 may be executed simultaneously (in parallel) with the processing of step S300 in the beam range extractor 304. Also, the processing of step S101 in the comparator 101 and the processing of step S300 in the beam range extractor 304 may be executed in reverse order.

Subsequently, the position determination region determiner 302 determines a position determination region for the CT image on the basis of the information of the comparison result output by the comparator 101. Further, the position determination region determiner 302 determines a preferential position determination region of the beam range on the basis of the information of the beam range output by the beam range extractor 304 (step S302). The position determination region determiner 302 outputs information indicating a range of the position determination region determined for the CT image and information indicating a range of the preferential position determination region to the position determiner 70.

Subsequently, the second image acquirer 60 acquires an X-ray fluoroscopic image PI of the inside of the body of the current patient P output by each radiation detector 30 (step S103). The second image acquirer 60 outputs the acquired X-ray fluoroscopic image PI to the position determiner 70.

Subsequently, the confirmation image generator 305 generates a confirmation image obtained by highlighting and superimposing the preferential position determination region output by the position determination region determiner 302 within the CT image output by the first image acquirer 50 (step S303). The confirmation image generator 305 outputs the generated confirmation image to the display controller 80. Thereby, the display controller 80 causes the display device 81 to display the confirmation image output by the confirmation image generator 305.

Subsequently, the position determiner 70 collates the CT image output by the first image acquirer 50 with the X-ray fluoroscopic image PI output by the second image acquirer 60 on the basis of information indicating the range of the preferential position determination region output by the position determination region determiner 302 and determines a position of the patient P (step S304). Further, the position determiner 70 obtains the amount of movement for moving the treatment table 10 to the determined position of the patient P. The position determiner 70 outputs information of the obtained amount of movement of the treatment table 10 to the bed controller 11. The processing of step S304 in the position determiner 70 may be executed simultaneously (in parallel) with the processing of step S303 in the confirmation image generator 305.

Subsequently, the bed controller 11 causes the treatment table 10 to be moved on the basis of the information of the amount of movement output by the position determiner 70 (step S105). Thereby, the position of the current patient P fixed on the treatment table 10 is moved to a position suitable for performing radiation treatment determined on the basis of the preferential position determination region.

As described above, like the medical image processing device 100 of the first embodiment, the medical image processing device 300 determines a position determination region for use in position alignment of the patient P with respect to a CT image output by the first image acquirer 50 with reference to a comparative image Ci collected in the comparative image database 110. Further, the medical image processing device 300 acquires information of a beam range of the treatment beam B from the CT image, extracts the beam range, and determines a preferential position determination region within the determined position determination region. The medical image processing device 300 outputs information indicating the range of the determined position determination region and information indicating the range of the preferential position determination region to the position determiner 70. Thereby, also in the medical image processing device 300, as in the medical image processing device 100 of the first embodiment, for example, it is possible to automatically set a position determination region similar to a region of interest used in position alignment of patients subjected to the treatment of the same treatment portion in the previous radiation treatment without designating a region of interest when the radiation treatment practitioner (the doctor or the like) operates the user interface such as the operator (not shown) to align the position of the patient P. Moreover, in the medical image processing device 300, because the beam range extractor 304 extracts the beam range from the CT image and the position determination region determiner 302 determines the preferential position determination region in consideration of the beam range to be used more preferentially in the position alignment of the patient P, it is possible to set a more valid position determination region than in the medical image processing device 100 of the first embodiment (a preferential position determination region for which position alignment is intensively required in radiation treatment). Thereby, in the medical device including the medical image processing device 300, the direction of the patient P to be treated in the radiation treatment can be directed to the position determined by the position determiner 70, i.e., the patient P can be directed in a direction suitable for radiating the treatment beam B. As described above, in the treatment system 3 provided with the medical device including the medical image processing device 300, the position determination for the patient P in the radiation treatment can be performed with higher accuracy.

Further, in the medical image processing device 300, the confirmation image generator 305 generates a confirmation image obtained by highlighting and superimposing the preferential position determination region on the CT image. Thereby, in the medical device including the medical image processing device 300, for example, the radiation treatment practitioner (the doctor or the like) can more clearly and visually confirm the region of interest to be used preferentially when the beam range is taken into consideration in the position alignment of the patient P.

Also, in the above description, the configuration in which the medical image processing device 100 of the first embodiment is replaced with the medical image processing device 300 has been described. In other words, the configuration in which the medical image processing device 300 is applied to the treatment system 1 provided with the medical device including the medical image processing device 100 of the first embodiment has been described. However, the medical image processing device 300 is not limited to the configuration with which the medical image processing device 100 of the first embodiment described above is replaced. For example, the medical image processing device 300 may be a configuration with which the medical image processing device 200 of the second embodiment is replaced. In this case, the beam range extractor 304 provided in the medical image processing device 300 extracts a beam range by acquiring information of the beam range of the treatment beam B from the CT image whose orientation is corrected by the patient orientation corrector 203 and the confirmation image generator 305 generates a confirmation image showing a preferential position determination region output by the beam range extractor 304 within the CT image whose orientation is corrected by the patient orientation corrector 203.

As described above, the medical image processing device 300 may further include the beam range extractor 304 configured to acquire information of a radiation range of radiation r radiated in the radiation treatment from the first image (a three-dimensional volume image (for example, a CT image)) and extract a prescribed radiation range including the radiation range whose information is acquired within the first image, wherein the position determination region determiner 302 may determine a second position determination region (a preferential position determination region) similar to the valid region Ea included within the first image within the prescribed radiation range including the radiation range.

As described above, the medical image processing device 300 may further include the confirmation image generator 305 configured to generate a confirmation image obtained by highlighting and superimposing a range of the preferential position determination region on the first image.

As described above, in the medical image processing device of each embodiment, according to a configuration of the comparator and the position determination region determiner, a position determination region for use in position alignment of the patient is determined with respect to a three-dimensional volume image with reference to a comparative image collected in the comparative image database. Thereby, in the medical device including the medical image processing device of each embodiment, it is possible to collate the three-dimensional volume image with the X-ray fluoroscopic image PI on the basis of the position determination region output by the medical image processing device and obtain an amount of movement for moving the treatment table to a position suitable for performing radiation treatment. In the treatment system provided with the medical device including the medical image processing device of each embodiment, the position determination of the patient can be performed with high accuracy at the time of radiation treatment.

Also, in each of the above-described embodiments, the case where a comparative image (a segment image or a valid region image) collected in the comparative image database is a three-dimensional image has been described. As described above, the valid region shown in the valid region image in this case is, for example, the region of interest designated by the radiation treatment practitioner (the doctor or the like) with respect to the three-dimensional volume image in the previous radiation treatment. However, the treatment system has a configuration in which, for example, the radiation treatment practitioner (the doctor or the like) designates a region of interest with respect to a DRR image. The comparative image in this case is a two-dimensional image. The valid region shown in the valid region image is also a two-dimensional region. However, even if the designated region of interest is a two-dimensional region, it is possible to show a valid region image by configuring a three-dimensional valid region on the basis of a two-dimensional region of interest if a condition in which an image serving as a source of the DRR image is captured, for example, a photography direction when the photography device captures the image or the like, is known. Thereby, the medical image processing device of each of the above-described embodiments can determine the position determination region as in each of the above-described embodiments and obtain the amount of movement for moving the treatment table to a position suitable for performing radiation treatment. Also, by increasing the number of viewpoints of the DRR image, in other words, by increasing the number of photography directions in which the image serving as the source of the DRR image is captured and increasing the number of DRR images, the accuracy when a three-dimensional valid region is created on the basis of the two-dimensional region of interest is improved. Thus, a plurality of valid region images in which a two-dimensional valid region is shown with respect to one three-dimensional segment image can be paired to form a comparative image, which can be collected in the comparative image database. In other words, in the comparative image database, a segment image in which a three-dimensional segment image and a two-dimensional valid region image described in each of the above-described embodiments are paired as well as a segment image in which a three-dimensional segment image and a three-dimensional valid region image described in each of the above-described embodiments are paired can be collected.

A medical image processing program for use in the medical image processing device described in the above-described embodiment is a medical image processing program for causing a computer to function as a medical image processing device including: a comparator configured to compare a first image obtained by photographing a patient with a comparative image which is an image used in previous radiation treatment and in which a valid region used in position alignment in the radiation treatment is designated; and a position determination region determiner configured to determine a position determination region similar to the valid region included within the first image on the basis of a comparison result of the comparator.

According to at least one embodiment described above, there are provided a comparator (101) configured to compare a three-dimensional volume image (a CT image) obtained by photographing a patient (P) with a comparative image (Ci) which is a three-dimensional volume image (a CT image) used in previous radiation treatment and in which a valid region (Ea) used in position alignment in the radiation treatment is designated; and a position determination region determiner (102) configured to determine a position determination region similar to the valid region (Ea) included within the three-dimensional volume image (the CT image) on the basis of a comparison result of the comparator (101), so that the position determination of the patient (P) can be performed with high accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing device comprising:
a comparator configured to compare a first image obtained by photographing a patient with a comparative image which is an image used in previous radiation treatment and in which a valid region used in position alignment in the radiation treatment is designated; and
a position determination region determiner configured to determine a position determination region similar to the valid region included within the first image on a basis of a comparison result of the comparator,
wherein the comparative image includes a plurality of comparative images collected in the previous radiation treatment, each of the comparative images including the valid region in which a part of each of segment images into which one fluoroscopic image used in the previous radiation treatment is segmented in a prescribed size is designated, and
wherein the position determination region determiner extracts a location similar to the valid region within the first image in each of the plurality of comparative images, combines locations extracted in the plurality of comparative images, and determines the position determination region.

2. The medical image processing device according to claim 1, further comprising a patient orientation corrector configured to correct an orientation of the first image to align an orientation of the patient shown in the first image with an orientation of a patient shown in the comparative image,
wherein the comparator compares the first image in which the orientation is corrected by the patient orientation corrector with the comparative image.

3. The medical image processing device according to claim 1,
wherein a plurality of comparative images are provided and the comparative images are grouped into a plurality of image groups for each treatment portion treated in the previous radiation treatment, and
wherein the comparator selects an image group of the comparative images to be compared with the first image in accordance with the treatment portion of the patient.

4. The medical image processing device according to claim 1, further comprising a range extractor configured to acquire information of a radiation range of radiation to be radiated in the radiation treatment from the first image and extract a prescribed range including the radiation range whose information is acquired within the first image,
wherein the position determination region determiner determines a second position determination region similar to the valid region included within the first image within the prescribed range including the radiation range.

5. The medical image processing device according to claim 4, further comprising a confirmation image generator configured to generate a confirmation image obtained by highlighting and superimposing a range of the second position determination region on the first image.

6. The medical image processing device according to claim 1, wherein the first image is a digitally reconstructed radiograph (DRR) image.

7. A medical device comprising:
the medical image processing device according to claim 1;
a first image acquirer configured to acquire the first image;
a second image acquirer configured to acquire a second image according to the radiation with which the patient is irradiated at a time point different from a photography time point of the first image from a photography device that performs a process of detecting the radiation that has been radiated using a detector and imaging the detected radiation; and
a position determiner configured to determine a position of the patient when the radiation treatment is performed on a basis of the position determination region using the first image and the second image.

8. The medical device according to claim 7, further comprising a display controller configured to cause a display device to display an image obtained by superimposing the position determination region on the first image.

9. A treatment system comprising:
the medical device according to claim 7;
an irradiator configured to irradiate a treatment portion of the patient with a treatment beam; and
a bed controller configured to control an amount of movement of a position of a bed on which the patient is fixed in alignment with a position determined by the position determiner.

10. A computer-readable non-transitory storage medium storing a medical image processing program for causing a computer to function as a medical image processing device comprising:
a comparator configured to compare a first image obtained by photographing a patient with a comparative image which is an image used in previous radiation treatment and in which a valid region used in position alignment in the radiation treatment is designated; and
a position determination region determiner configured to determine a position determination region similar to the valid region included within the first image on a basis of a comparison result of the comparator,
wherein the comparative image includes a plurality of comparative images collected in the previous radiation treatment, each of the comparative images including the valid region in which a part of each of segment images into which one fluoroscopic image used in the previous radiation treatment is segmented in a prescribed size is designated, and
wherein the position determination region determiner extracts a location similar to the valid region within the first image in each of the plurality of comparative images, combines locations extracted in the plurality of comparative images, and determines the position determination region.

* * * * *